(12) United States Patent
Herz et al.

(10) Patent No.: US 7,576,090 B2
(45) Date of Patent: Aug. 18, 2009

(54) BENZAZOLE ANALOGUES AND USES THEREOF

(75) Inventors: Thomas Herz, Stockdorf (DE); Rolf Krauss, Planegg-Martinsried (DE); Michael Kubbutat, Schallstadt (DE); Martin Lang, Graefelfing (DE); Christoph Schaechtele, Freiburg (DE); Stefan Tasler, Seefeld-Hechendorf (DE); Frank Totzke, Freiburg (DE)

(73) Assignee: 4SC AG, Martinsried (DE)

( * ) Notice: Subject to any disclaimer, the term of this patent is extended or adjusted under 35 U.S.C. 154(b) by 545 days.

(21) Appl. No.: 11/317,909

(22) Filed: Dec. 22, 2005

(65) Prior Publication Data

US 2006/0142570 A1    Jun. 29, 2006

Related U.S. Application Data

(60) Provisional application No. 60/640,024, filed on Dec. 27, 2004.

(51) Int. Cl.
*A61K 31/517* (2006.01)
*A61K 31/519* (2006.01)
*A61K 31/52* (2006.01)
*C07D 487/00* (2006.01)
*C07D 239/70* (2006.01)

(52) U.S. Cl. ............ 514/263.2; 514/258.1; 514/262.1; 514/263.1; 544/256; 544/253

(58) Field of Classification Search ............... 544/253, 544/256; 514/258.1, 262.1, 263.1, 263.2
See application file for complete search history.

(56) References Cited

FOREIGN PATENT DOCUMENTS

| WO | WO 00/41669 A | 7/2000 | | |
|---|---|---|---|---|
| WO | WO 02/44156 A | 6/2002 | | |
| WO | WO 03/074515 A | 9/2003 | | |
| WO | WO 03/082272 | * 10/2003 | ................ | 548/200 |
| WO | WO 2004/085425 | 10/2004 | | |
| WO | WO 2004/030140 A | 4/2005 | | |
| WO | WO 2005/030140 | * 4/2005 | ................ | 548/400 |

OTHER PUBLICATIONS

Abuzar et al. Synthesis of 2,5(6)-disubstituted benzimitadoles. Chemical Abstracts + Indexes, 1996, p. 731, vol. 28, No. 105, American Chemical Society, Columbus, USA.

* cited by examiner

*Primary Examiner*—Kamal A Saeed
*Assistant Examiner*—Samantha L Shterengarts
(74) *Attorney, Agent, or Firm*—Baker, Donelson, Bearman, Caldwell & Berkowitz, PC

(57) ABSTRACT

The present invention relates to compounds of the general formulas (I), (Ia) and (II) and salts and physiologically functional derivatives thereof,

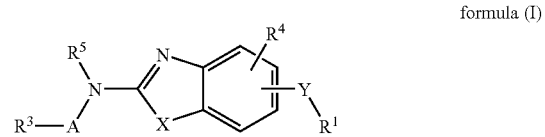

formula (I)

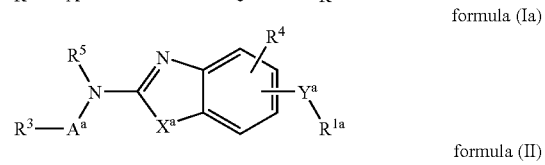

formula (Ia)

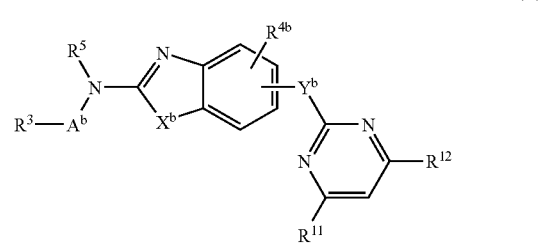

formula (II)

wherein
the substituents —Y are attached to the 5- or 6-position of the benzazole.

11 Claims, No Drawings

BENZAZOLE ANALOGUES AND USES THEREOF

The present invention relates to benzazoles of the general formula (I) or a salt or a physiologically functional derivative or a stereoisomer thereof, for use as a medicament. The compounds of the invention are exceptionally useful for the treatment of diseases associated with abnormal and hyperproliferation of cells in a mammal, especially humans. In particular, they are useful for the treatment of all forms of cancer. Furthermore a process of preparing said benzazole derivatives is disclosed.

BACKGROUND OF THE INVENTION

Protein kinases play a central role in the regulation of cellular functions. This includes processes like cell growth and division, cell differentiation and cell death, but also many other cellular activities. Protein kinases catalyze the transfer of phosphate residues from ATP on target proteins which as a consequence of this protein kinase mediated phosphorylation change their three-dimensional structure and thereby their physiological function. Depending on the amino acid which becomes phosphorylated by a protein kinase these enzymes are grouped in two families, the so-called serine/threonine protein kinases and the tyrosine protein kinases.

Based on the human genome project it is; known that in human beings there exist 518 DNA sequences which encode for a protein kinase-like protein sequence. In the last about 20 years for several of these 518 proteins it, could be shown t modifications in their related gene sequences (e.g. point mutations, deletions or gene amplifications) result in pathological changes of the cellular activities of the corresponding protein kinase. This is in particular true for protein kinases which are involved in cell proliferation and cell cycle control, in survival of cells and cell death, in tumor angiogenesis, and in formation of tumor metastases.

Several so-called oncogenes are pathologically modified genes which in their protooncogenic form encode for protein kinases involved in normal, physiological regulation of cell growth and division.

Since protein kinases are key regulators of cell functions and since they can show dysregulated enzymatic activity in cells they are promising targets for the development of therapeutic agents. There are many ongoing drug discovery projects in the pharmaceutical industry with the goal to identify modulators of protein kinases. The major focus is currently on protein kinases involved in inflammation and cancer, but besides this protein kinases are currently discussed as promising targets in almost every disease area.

In the tumor field the first protein kinase inhibitors (Gleevec, Iressa) have already reached the market. In addition, a great number of protein kinase inhibitors are currently in various phases of clinical development In most cases these compounds are either targeting subtypes of the EGF (Epidermal Growth Factor) receptor or of the VEGF (Vascular Endothelial Growth Factor) receptor. All these compounds have been developed with the goal to specifically inhibit one particular protein kinase, for which there is evidence that it interferes with one of the four major molecular processes of tumor progression. These four processes are (1) cell proliferation/cell cycle control, (2) regulation of programmed cell death (apoptosis) and cell survival, (3) tumor angiogenesis and (4) tumor metastasis. The present invention relates to benzazole derivatives which may be useful for inhibition of protein kinases involved in diseases besides cancer, but which are especially useful as anti-tumor agents. This includes monospecific protein kinase inhibitors, which preferentially inhibit one protein kinase which is causatively involved in tumor progression, but also so-called multi-target protein kinase inhibitors, which inhibit at least two different protein kinases which play a role in two or more different molecular mechanism of tumor progression As an example, such a compound could be an inhibitor of tumor angiogenesis and, in addition, also a stimulator of apoptosis.

The concept of multi-target protein kinase inhibitors is a new approach although the idea of developing "multiplex protein kinase inhibitors" has already been described by J. Adams et al., Current Opinion in Chemical Biology 6, 486-492, 2002. Therein compounds are described, which, at the same time, inhibit several protein kinases, which however all are involved in one molecular mechanism of tumor progression, namely tumor angiogenesis.

In WO 2004085425 benzazoles are described as kinase inhibitors. In WO 9924035 2-aminobenzothiazoles are described. The compounds have also been published in Das et al., Bioorg. Med. Chem. Lett 13, 2003, 2587-2590 and in Das et al., Bioorg. Med. Chem. Lett 13, 2003, 2145-2149. In WO 2000061580 benzimidazolyl- and benzoxazolylacetylaminopyridylbutyrates are described as integrin antagonists. In WO 9940072 five-membered, benzo-condensed heterocycles used as antithrombotics of are described.

The object of the present invention is solved by the teaching of the independent claims. Further advantageous features, aspects: and, details of the invention are evident from the dependent claims, the description, the us, and the examples of the present application. Considering the lack of currently available treatment options for the majority of the conditions associated with protein kinases, like ABL1, ACV-R1, AKT1, AKT2, AKT-3, ARK5, Aurora-A, Aurora-B, Aurora-C, B-RAF, BRK, CDC42BPB, CDK1, CDK2, CDK3, CDK4, CDK5, CDK6, CDK7, CDK9, CHK1, CK2, COT, CSK, DAPK1, EGF-R EPHA1, EPHA2, EPHA4, EPHB1, EPHB2, EPHB3, EPHB4, ERBB2, ERBB4, FAK, FGF-R1, FGF-R3, FGF-R4, FGR, FLT3, GSK3-beta, HCK, IGF1-R, IKK-beta, IKK-epsilon, INS-R, IRAK4, ITK, JAK2, JAK3, JNK3, KIT, LCK, LYN, MAPKAPK5, MET, MST4, MUSK, NEK2, NEK6, NLK, PAK1, PAK2, PAK4, PBX, PCTAIRE1, PDGFR-alpha, PDGFR-beta, PDK1, PIM1, PIM2, PKC-alpha, PKC-beta1, PKC-beta2, PKC-delta, PKC-epsilon, PKC-eta, PKC-gamma, PKC-iota, PKC-mu, PKC-theta, PKC-zeta, PLK1, PRK1, RET, ROCK2, S6K, SAK, SGK1, SGK3, SNK, SRC, SRPK2, SYK, TGFB-R1, TIE2, TSF1, TSK2, TTK, VEGF-R1, VEGF-R2, VEGF-R3, VRK1, WEE1, YES, ZAP70 especially with protein kinases Mike EGF-R (cell proliferation), ERBB2 (cell proliferation), PDGFR (cell proliferation), FLT3 (cell proliferation), Aurora-A (cell cycle control), Aurora-B (cell cycle control), IGF1-R (apoptosis), VEGF-R2 (angiogenesis), VEGF-R3 (angiogenesis), TIE2 (angiogenesis), EPHB4 (angiogenesis), FAK (metastasis), and SRC kinase (metastasis), there is still a great need for new therapeutic agents that inhibit these protein targets.

Herein described benzazole derivatives are a new group of protein kinase inhibitors which show differential inhibition of protein kinases, each of which can be, assigned to one of the four molecular mechanism of tumor development.

The present invention relates to compounds of the general formula (I) or a salt or a physiologically functional derivative or a stereoisomer thereof,

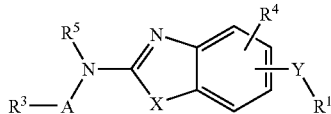

formula (I)

wherein the substituent —Y—R¹ is attached to the 5- or 6-position of the benzazole;

x independently represents S, O, SO, or $SO_2$,

Y independently represents S, O, $NR^2$, SO, or $SO_2$;

A independently represents ←CO—, ←CS—, ←SO—, ←$SO_2$—, ←$CO_2$—, ←$CONR^8$—, ←$NR^8CO$—, ←$NR^8CONR^9$—; ←$NR^8COO$—, ←$NR^8NR^9CO$—, ←$NR^8OCO$—, ←$ONR^8CO$—, or ←$NR^8SO_2$—, where ← indicates the point of attachment to $R^3$;

$R^2$ independently represents H, alkyl, cycloalkyl, —$COR^6$, —$SOR^6$, —$SO_2R^6$, —CN, hydroxyalkyl, haloalkyl, or haloalkyloxy;

$R^3$ independently represents H, alkyl, cycloalkyl, aryl, or heteroaryl;

$R^4$ independently represents H, —$COR^6$, —$CO_2R^6$, —$SOR^6$, —$SO_2R^6$, —$SO_3R^6$, —$NO_2$, —CN, —$CF_3$, —$OCH_3$, —$OCF_3$, alkyl, cycloalkyl, alkoxy, —$NH_2$, alkylamino, —$NR^7COR^6$, halogen, —OH, —SH, alkylthio, haloalkyl, haloalkyloxy, aryl or heteroaryl;

$R^5$ independently represents H, alkyl, cycloalkyl, —$COR^6$, —$SOR^6$, —$SO_2R^6$, —CN, hydroxyalkyl, haloalkyl, haloalkyloxy, aryl, or heteroaryl;

$R^{6a}$ independently represents H, alkyl, cycloalkyl, —$NR^8NR^2R^9$, —$ONR^8R^9$, —$NR^8OR^9$, aryl or heteroaryl;

$R^6$ independently represents H, alkyl, cycloalkyl, —$NR^8R^9$, —$NR^8NR^2R^9$, —$ONR^8R^9$, —$NR^8OR^9$, aryl or heteroaryl;

$R^7$ independently represents H, alkyl, cycloalkyl or alkoxy;

$R^8$ independently represents H, alkyl, cycloalkyl, —$COR^6$, —$SOR^6$, —$SO_2^6$, haloalkyl, haloalkyloxy, aryl or heteroaryl;

$R^9$ independently represents H, alkyl, cycloalkyl, —$COR^6$, —$SOR^6$, —$SO_2R^6$, haloalkyl, haloalkyloxy, aryl or heteroaryl;

$R^1$ independently represents one of the allowing groups:

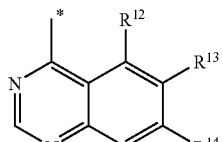

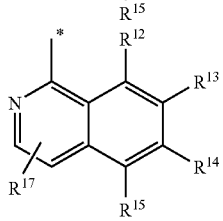

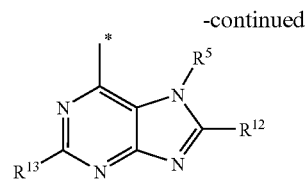

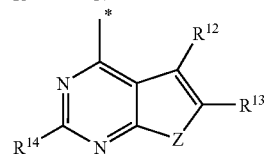

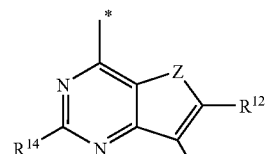

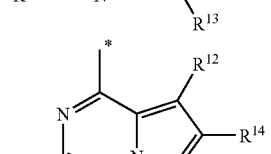

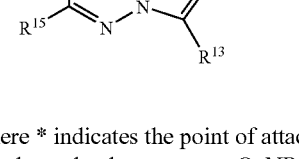

where * indicates the point of attachment;

Z independently represents O, $NR^8$, or S;

$R^{12}$ independently represents H, halogen, nitro, trifluoromethyl, alkyl, aryl, heteroaryl, —$NR^{8a}R^{9a}$, or —$X^2R^{16}$;

$R^{8a}$ independently represents H, alkyl, cycloalkyl, —$COR^{6a}$, —$SOR^6$, —$SO_2R^6$, haloalkyl, haloalkyloxy, aryl or heteroaryl;

$R^{9a}$ independently represents H, alkyl, cycloalkyl, —$COR^{6a}$, —$SOR^6$, —$SO_2R^6$, haloalkyl, haloalkyloxy, aryl or heteroaryl;

$R^{13}$ independently represents H, halogen, nitro, trifluoromethyl, alkyl, aryl, heteroaryl, —$NR^{8a}R^{9a}$, or —$X^2R^{16}$;

$R^{14}$ independently represents H, halogen, nitro, trifluoromethyl, alkyl, aryl, heteroaryl, —$NR^{8a}R^{9a}$, or —$X^2R^{16}$;

$R^{15}$ independently represents H, halogen, nitro, trifluoromethyl, alkyl, aryl, heteroaryl, —$NR^{8a}R^{9a}$, or —$X^2R^{16}$;

$R^{17}$ independently represents H, halogen, nitro, trifluoromethyl, alkyl, aryl, heteroaryl, —$NR^{8a}R^{9a}$, or —$X^2R^{16}$;

$X^2$ independently represents a direct bond, —O—, —$CH_2$—, —OCO—, carbonyl, —S—, —SO—, —$SO_2$—, —$NR^8CO$—, —$CONR^8$—, —$SO_2NR^8$—, —$NR^8SO_2$— or —$NR^{8a}$—;

$R^{16}$ independently represents H, alkyl, cycloalkyl, —$SOR^6$, —$SO_2R^6$, —$OCH_3$, hydroxyalkyl, haloalkyl, haloalkyloxy, or one of the following groups:

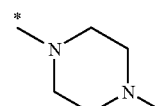 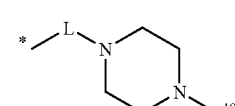

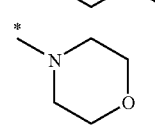 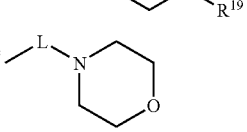

-continued

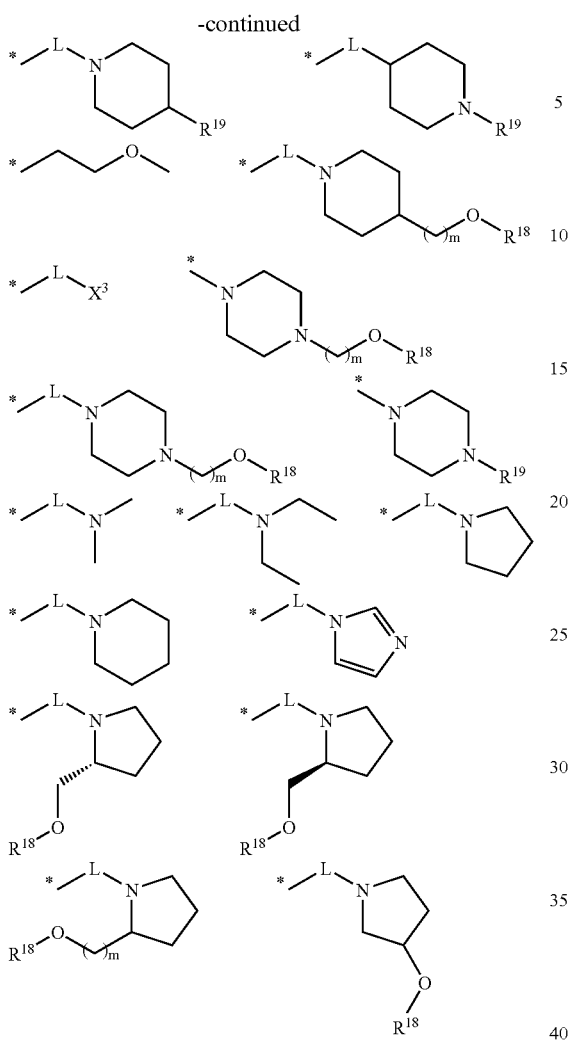

where * indicates the point of attachment;
m independently represents an integer from 1-3;
L is absent or represents a divalent linkage group selected from alkylen, cycloalkylen, heterocyclylen, arylen, or heteroarylen, wherein one or more of the (—CH$_2$—) groups may be replaced by an oxygen or a NR$^8$, and wherein one or more carbon atoms may be independently substituted by one or two substituents selected from halogen, hydroxy, alkoxy, halo-alkyloxy, phoshonooxy, or phoshonooxyalkyl;
X$^3$ independently represents —COOH, —COOalkyl, —OH, —SH, —SO$_3$H, or —SO$_2$NR$^8$R$^9$;
R$^{18}$ independently represents H, phosphonooxy, or phosphonooxyalkyl;
R$^{19}$ independently represents H, alkyl, cycloalkyl, alkylamino, or alkoxy;

with the proviso that the following compounds are excluded:
N-[6-(6,7-Dimethoxy-quinolin-4-yloxy)-5-fluoro-benzothiazol-2-yl]-2-phenyl-acetamide
N-[6-(6,7-Dimethoxy-quinolin-4-yloxy)-benzothiazol-2-yl]-2-phenyl-acetamide, N-[6-(6,7-Dimethoxy-quinolin-4-yloxy)-5-fluoro-benzothiazol-2-yl]-3-phenyl-propionamide, N-[6-6,7-Dimethoxy-quinolin-4-yloxy)-5-fluoro-benzothiazol-2-yl]-2-(3-trifluoromethyl-phenyl)-acetamide, 2-(3,5-Bis-trifluoromethyl-phenyl)-N-[6-(6,7-dimethoxy-quinolin-4-yloxy)-5-fluoro-benzothiazol-2-yl]-acetamide, 2-(2-Chloro-5-trifluoromethyl-phenyl)-N-[6-(6,7-dimethoxy-quinolin-4-yloxy)-5-fluoro-benzothiazol-2-yl]-acetamide;

an alkyl group, if not stated otherwise, denotes a linear or branched C$_1$-C$_6$-alkyl, preferably a linear or branched chain of one to five carbon atoms, a linear or branched C$_2$-C$_6$-alkenyl or a linear or branched C$_2$-C$_6$-alkynyl group, which can be substituted by one or more substituents R';
the C$_1$-C$_6$-alkyl, C$_2$-C$_6$-alkenyl and C$_2$-C$_6$-alkynyl residue may be selected from the group comprising —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R')$_3$, —C$_2$(R')$_5$, —CH$_2$—C(R')$_3$, —C$_3$(R')$_7$, —C$_2$H$_4$—C(R')$_3$, —C$_2$H$_4$—CH=CH$_2$, —CH=CH—C$_2$H$_3$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH=C(CH$_3$)$_2$, —CH$_2$—CH=C(CH$_3$)$_2$, —C(CH$_3$)=C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡CH—CH—CH$_3$, —CH=CH—C≡C—CH$_3$, —C≡C—C≡C—CH$_3$, —C≡C—CH$_2$—CH=CH$_2$, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C(CH$_3$)$_2$, —C$_2$H$_4$—CH=C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, —C$_2$H$_4$—C≡C—C$_2$H$_5$;

R' independently represents H, —CO$_2$R", —CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
R" independently represents H, haloalkyl, hydroxyalkyl, alkyl, cycloalkyl, aryl heteroaryl or aminoalkyl;

an alkylene group denotes a divalent linear or branched C$_1$-C$_6$alkylene, preferably a linear or branched chain of one to five carbon atoms, a, linear or branched C$_2$-C$_6$-alkylene or a linear or branched C$_2$-C$_6$-alkynylene group, which may be substituted by one or more substituents R';

a cycloalkylene group denotes a divalent non-aromatic ring system containing three to eight carbon atoms, preferably four to eight, carbon atoms, wherein one or more of the carbon atoms in the ring may be substituted by a group E, E being O, S, SO, SO$_2$, N, or NR", R" being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group having five to fifteen carbon atoms, which may be substituted by one or more substituents R', and may be fused to another aromatic ring, where R' is as defined above;

a heteroarylene group denotes a divalent, 5- or 6-membered heterocyclic group which contains at least one heteroatom selected from O, N, and S, wherein the heterocyclylene group may be fused to another aromatic ring and may be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring can be substituted by a group E, E being O, S, SO, SO$_2$, N, or NR", R" being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, CR$^{10}$(R$^{10'}$)R$^{10''}$, —C$_2$(R$^{10}$)$_5$, —CH$_2$—C(R$^{10}$)$_3$, —CH$_2$—CR$^{10}$(R$^{10'}$)$_2$, —CH$_2$—CR$^{10}$(R$^{10'}$)R$^{10''}$, —C$_3$(R$^{10}$)$_7$, or —C$_2$H$_4$—C(R$^{10}$)$_3$, wherein R$^{10}$, R$^{10'}$, R$^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10''}$, —OC$_3$(R$^{10}$)$_7$ or —OC$_2$H$_4$—C(R$^{10}$)$_3$, wherein R$^{10}$, R$^{10'}$, R$^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents: R', where R' is as defined above; the aryl group is preferably a phenyl group, -o-$C_6H_4$—R', -m-$C_6H_4$—R', -p-$C_6H_4$—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring.

For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phtalazine, pteridine, thiatetraazaindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group. This heterocyclic group can be substituted by one or more substituents R', wherein R' is as defined above;

a phosphonooxy group is —O—P(=O)(OH)$_2$ or a salt thereof;

a phosphonooxyalkyl group denotes an -allyl-O—P(=O)(OH)$_2$ group or a salt thereof, alkyl being as defined above.

The present invention also relates to compounds of the general formula (Ia) or a salt or a physiologically functional derivative or a stereoisomer thereof,

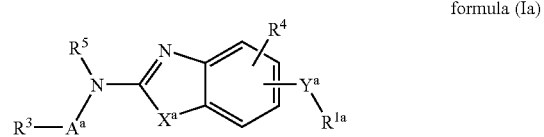

formula (Ia)

wherein the substituent —Y—R$^{1a}$ is attached to the 5- or 6-position of the benzazole;

X$^a$ independently represents S, O, SO, or SO$_2$;

Y$^a$ independently represents S, NR$^2$, SO, or SO$_2$;

A$^a$ independently represents ←CO—, ←CS—, ←SO—, ←SO$_2$—, ←CO$_2$—, ←CONR$^8$—, ←NR$^8$CO—, ←NR$^8$CONR$^9$—; ←NR$^8$COO—, ←NR$^8$NR$^9$CO—, ←NR$^8$OCO—, ←ONR$^8$CO—, or ←NR$^8$SO$_2$—, where, ← indicates the point of attachment to R$^3$;

$R^{1a}$ independently represents one of the following groups:

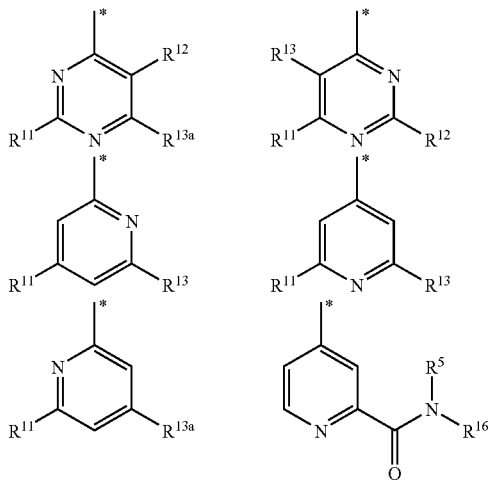

where * indicates the point of attachment;
$R^{11}$ independently represents H, —NHR$^{8a}$, or one of e groups:

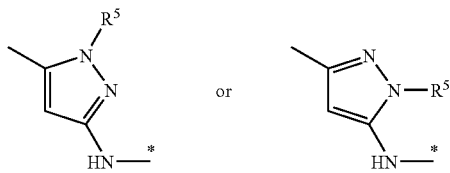

where * indicates the point of attachment,
$R^{13a}$ independently represents H, halogen, nitro, trifluoromethyl, alkyl, —NR$^{8a}$R$^{9a}$, or —X$^2$R$^{16}$;
$R^2$, $R^3$, $R^4$, $R^5$, $R^6$, $R^{6a}$, $R^7$, $R^8$, $R^{8a}$, $R^9$, $R^{9a}$, $R^{12}$, $R^{13}$, $R^{16}$, or $X^2$, are as hereinbefore defined;

an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkinyl group, which can be substituted by one or more substituents R';
the $C_1$-$C_6$-alkyl, $C_2$-$C_6$-alkenyl and $C_2$-$C_6$-alkinyl residue may be selected from the group comprising —CH$_3$, C$_2$H$_5$, —CH═CH$_2$, —C≡CH, —C$_3$H$_7$, —CH(CH$_3$)$_2$, —CH$_2$—CH═CH$_2$, —C(CH$_3$)═CH$_2$, —CH═CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R')$_3$, —C$_2$(R')$_5$, —CH$_2$—C(R')$_3$, —C$_3$(R')$_7$, —C$_2$H$_4$—C(R')$_3$, —C$_2$H$_4$—CH═CH$_2$, —CH═CH—C$_2$H$_5$, —CH═C(CH$_3$)$_2$, —CH$_2$—CH═CH—CH$_3$, —CH═CH—CH═CH$_2$, —C$_2$H$_4$—C≡CH, —C≡C—C$_2$H$_5$, —CH$_2$—C≡C—CH$_3$, —C≡C—CH═CH$_2$, —CH═CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH═CH$_2$, —CH═CH—C$_3$H$_7$, —C$_2$H$_4$—CH═CH—CH$_3$, —CH$_2$—CH═CH—C$_2$H$_5$, —CH$_2$—CH═CH—CH═CH$_2$, —CH═CH—CH═CH—CH$_3$, —CH═CH—CH$_2$—CH═CH$_2$, —C(CH$_3$)═CH—CH═CH$_2$, —CH═C(CH$_3$)—CH═CH$_2$, —CH═CH—C(CH$_3$)═CH$_2$, —C(CH$_3$)═CH—C≡CH, —CH═C(CH$_3$)—C≡CH, —CH═C—C≡CH, —CH$_2$—CH═C(CH$_3$)$_2$, C(CH$_3$)═C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH═CH$_2$, —CH$_2$—CH═CH—C≡CH, —CH$_2$—C≡C—C≡CH, —C≡C—CH═CH—CH$_3$, —CH═CH—C≡C—CH$_3$, —C≡C—C≡C—CH$_3$, —C≡C—CH$_2$—CH═CH$_2$, —CH═CH—CH$_2$—C≡CH, —C≡C—CH$_2$—C≡CH, —C(CH$_3$)═CH—CH═CH$_2$, —CH═C(CH$_3$)—CH═CH$_2$, —CH═CH—C(CH$_3$)═CH$_2$, —C(CH$_3$)═CH—C≡CH, —CH═C(CH$_3$)—C≡CH, —C≡C—C(CH$_3$)═CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH═CH$_2$, —CH═CH—C$_4$H$_9$, —C$_3$H$_6$—CH═CH—CH$_3$, —CH$_2$—CH═CH—C$_3$H$_7$, —C$_2$H$_4$—CH═CH—C$_2$H$_5$, —CH$_2$—C(CH$_3$)═C(CH$_3$)$_2$, —C$_2$H$_4$—CH═C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, —C$_2$H$_4$—C≡C—C$_2$H$_5$;

R' independently represents H, —CO$_2$R", CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" independently represents H, haloalkyl, hydroxyalkyl, cycloalkyl, aryl, heteroaryl or aminoalkyl;

an alkylene group denotes a divalent linear branched $C_1$-$C_6$-alkylene, preferably a linear or branched chain of one to five carbon atoms a linear or branched $C_2$-$C_6$-alkenylene or a linear or branched $C_2$-$C_6$-alkynylene group, which may be substituted by one or more substituents R';

a cycloalkylene group denotes a divalent, non-aromatic ring system containing three to eight carbon atoms, preferably four to eight, carbon atoms, wherein one or more of the carbon atoms in the ring may be substituted by a group E, E being O, S, SO, SO$_2$, N, or NR", R" being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group hang five to fifteen carbon atoms, which may be substituted by one or more substituents R', and may be fused to another aromatic ring, where R' is as defined above;

a heteroarylene group denotes a divalent 5- or 6-membered heterocyclic group which contains at least one heteroatom select from O, N, and S, wherein the heterocyclylene group may be fused to another aromatic ring and may be substituted by one or more substituents R', wherein R' is as defined above;, a cycloalkyl group denotes a non-aromatic ring system containing three to eight carbon atoms, preferably four to eight carbon atoms, wherein one or more of the carbon atoms in the ring can be substituted by a group E, E being O, S, SO, SO$_2$, N, or NR", R" being as defined above; the $C_3$-$C_8$-cycloalkyl residue may be selected from the group comprising -cyclo-$C_3$H$_5$, -cyclo-$C_4$H$_7$, -cyclo-$C_5$H$_9$, -cyclo-$C_6$H$_{11}$, -cyclo-$C_7$H$_{13}$, -cyclo-$C_8$H$_{15}$, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C($R^{10}$)$_3$, —C$R^{10}$($R^{10'}$)$_2$, —C$R^{10}$($R^{10'}$)$R^{10''}$, —C$_2$($R^{10}$)$_5$, —CH$_2$—C($R^{10}$)$_3$, —CH$_2$—C$R^{10}$($R^{10'}$)$_2$, —CH$_2$—C$R^{10}$($R^{10'}$)$R^{10''}$, —C$_3$($R^{10}$)$_7$, or —C$_2$H$_4$—C($R^{10}$)$_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —OC$R^{10}$($R^{10'}$)$_2$, —OC$R^{10}$($R^{10'}$)$R^{10''}$, —OC$_2$($R^{10}$)$_5$, —OCH$_2$—C($R^{10}$)$_3$, —OCH$_2$—C$R^{10}$($R^{10'}$)$_2$, —OCH$_2$—C$R^{10}$($R^{10'}$)$R^{10''}$, —OC$_3$($R^{10}$)$_7$ or —OC$_2$H$_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R', where R' is as defined above; the aryl group is preferably a phenyl group, -o-C$_6$H$_4$—R', -m-C$_6$H$_4$—R', -p-C$_6$H$_4$—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group. This heterocyclic group can be substituted by one or more substituents R', wherein R' is as defined above;

a phosphonooxy group is —O—P(=O)(OH)$_2$ or a salt thereof;

a phosphonooxyalkyl group denotes an -alkyl-O—P(=O)(OH)$_2$ group or a salt thereof, alkyl being as defined above.

The present invention also relates to compounds of the general formula (II) or a salt or a physiologically functional derivative or a stereoisomer thereof,

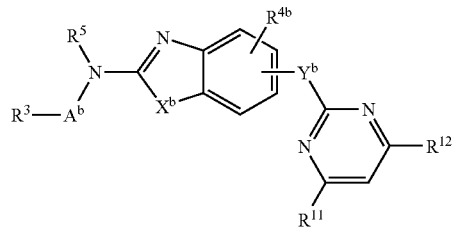

formula (II)

wherein the substituent —$Y^b$— is attached to the 5- or 6-position of the benzazole;

$X^b$ independently represents S, O, SO, or SO$_2$;

$Y^b$ independently represents S, NR$^2$, SO, or SO$_2$;

$A^b$ independently represents ←CO—, ←CS—, ←SO—, ←SO$_2$—, ←CO$_2$—, ←CONR$^8$—, ←NR$^8$CO—, ←NR$^8$CONR$^9$—; ←NR$^8$COO—, ←NR$^8$NR$^9$CO—, ←NR$^8$OCO—, ←ONR$^8$CO—, or ←NR$^8$SO$_2$—, where ← indicates the point of attachment to R$^3$;

$R^{4b}$ independently represents H, —SOR$^6$, —SO$_2$R$^6$, —SO$_3$R$^6$, —NO$_2$, —CN, —CF$_3$, —OCH$_3$, —OCF$_3$, alkyl, cycloalkyl, alkoxy, —NH$_2$, alkylamino, —NR$^7$COR$^6$, halogen, —OH, —SH, alkylthio, haloalkyl, haloalkyloxy, aryl or heteroaryl;

$R^2$, $R^3$, $R^5$, $R^6$, $R^{6a}$, $R^7$, $R^8$, $R^{8a}$, $R^9$, $R^{9a}$, $R^{11}$, $R^{12}$, $R^{16}$, $X^2$ are as hereinbefore defined;

an alkyl group, if not stated otherwise, denotes a linear or branched alkyl group, preferably a linear or branched chain of one to five carbon atoms, a linear or branched C$_2$-C$_6$-alkenyl or a linear or branched C$_2$-C$_6$-alkinyl group, which can be substituted by one or more substituents R', the C$_1$-C$_6$-alkyl, C$_2$-C$_6$-alkenyl and C$_2$-C$_6$-alkinyl residue may be selected from the group comprising —CH$_3$, —C$_2$H$_5$, CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R')$_3$, —C$_2$(R')$_5$, —CH$_2$—C(R')$_3$, —C$_3$(R')$_7$, —C$_2$H$_4$—C(R')$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH$_2$—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)CH$_2$, —CH$_2$—CH=C(CH$_3$)$_2$, C(CH$_3$)=C(CH$_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —$CH_2$—CH=C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

R' independently represents H, —$CO_2$, —CONHR", —CR"O, —$SO_2$NR", —NR"—CO-haloalkyl, —$NO_2$, —NR"-$SO_2$-haloalkyl, —NR"-$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" independently represents H, haloalkyl, hydroxyalkyl, alkyl, cycloalkyl, aryl, heteroaryl or aminoalkyl;

an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

a cycloalkylene group denotes a divalent non-aromatic ring system containing three to eight carbon atoms, preferably four to eight carbon atoms, wherein one or more of the carbon atoms in the ring may be substituted by a group E, E being O, S, SO, $SO_2$, N, or NR", R" being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group having five to fifteen carbon atoms, which may be substituted by one or more substituents R', and may be fused to another aromatic ring, where R' is as defined above;

a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring can be substituted by a group E, E being O, S, SO, $SO_2$, N, or NR", R" being as defied above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

an alkoxy group denotes an O-alkyl group, the alkyl group being as defined above, the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C($R^{10}$)$_3$, —C$R^{10}$($R^{10'}$)$_2$, —C$R^{10}$($R^{10'}$)$R^{10"}$, —$C_2$($R^{10}$)$_5$, —$CH_2$—C($R^{10}$)$_3$, —$CH_2$—C$R^{10}$($R^{10'}$)$_2$, —$CH_2$—, C$R^{10}$($R^{10'}$)$R^{10"}$, —$C_3$($R^{10}$)$_7$, or —$C_2H_4$—C($R^{10}$)$_3$, wherein $R^{10}$, $R^{10'}$, $R^{10"}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the all group being as defined above; the haloalkyloxy group is preferably a —OC($R^{10}$)$_3$, —OC$R^{10}$($R^{10'}$)$_2$, —OC$R^{10}$($R^{10'}$)$R^{10"}$, —$OC_2$($R^{10}$)$_5$, —$OCH_2$—C($R^{10}$)$_3$, —$OCH_2$—C$R^{10}$($R^{10'}$)$_2$, —$OCH_2$—C$R^{10}$($R^{10'}$)$R^{10"}$, —$OC_3$($R^{10}$)$_7$ or —$OC_2H_4$—C($R^{10}$)$_3$, wherein $R^{10}$, $R^{10'}$, $R^{10"}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R', where R' is as defined above; the aryl group is preferably a phenyl group, -o-$C_6H_4$—R', -m-$C_6H_4$—R', -p-$C_6H_4$—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl; 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-1-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolyl, purine, phthalazine, pteridine, thiatetraazaindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group.

This heterocyclic group can be substituted by one or more substituents R', wherein R' is as defined above;

a phosphonooxy group is —O—P(=O)(OH)$_2$ or a salt thereof;

a phosphonooxyalkyl group denotes an alkyl-O—P(=O)(OH)$_2$ group or a salt thereof, alkyl being as defined above.

The invention also provides a pharmaceutical composition comprising a compound of formula (I), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

Prodrugs of the compounds of the present invention include but are not limited to: esters, which are transformed in vivo into the corresponding active alcohol, esters, which are transformed in vivo into the corresponding active acid, imines, which are transformed in vivo into the corresponding amines, imines which are metabolized in vivo into the corresponding active carbonyl derivative (e.g. aldehyde or ketone), 1-carboxy-amines, which are decarboxylated in vivo into the active amine, phosphoryloxy-compounds, which are dephosporylated in vivo by phosphateases into the active alcohols, and amides which are metabolized into the corresponding above amine or acid respectively.

The term "stereoisomer" as used herein refers to compound with at least one stereogenic center, which can be R— or S-configurated. It has to be understood, that in compounds with more than one stereogenic center each of which independently from each other can be R— or S-configurated. The term "stereoisomer" as used herein also refers to salts of the compounds herein described with optically active acids or bases.

In addition, the present invention provides methods for preparing the compounds of the invention such as compounds of formula (I).

The compounds of formula (I), formula (Ia), and formula (II) may be obtained via various methods. One possibility for the synthesis of compounds of formula (I) comprises the step of reacting a compound of formula (VII), wherein R$^3$, R$^4$, R$^5$, A, X, and Y are defined above in formula (I), formula (Ia) and formula (II), with a compound of formula (VII), wherein R$^1$ is as defined above and LG comprises a leaving group such as Cl, Br, and I.

Either nucleophilic substitution or palladium-catalyzed cross-coupling may be applied. If Y=NR$^2$, R$^2$ may be added before or after addition of R$^1$.

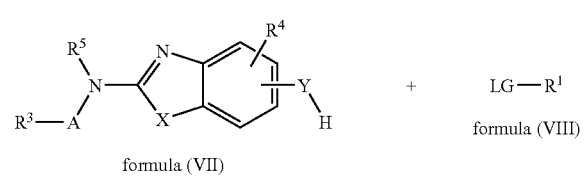

formula (VII)

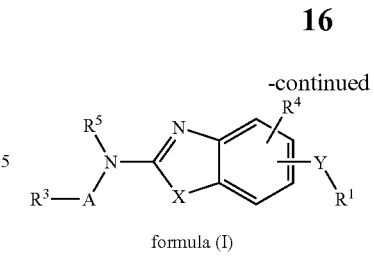

formula (I)

Another way to synthesize compounds of formula (I), formula (Ia) and formula (II) comprises the step of adding, a R$^5$ to a compound of formula (IX), wherein R$^1$, R$^4$, X, and Y are as defined above in formula (I), formula (Ia) and formula, (II), followed by reaction with an acid chloride, a carboxylic acid, a sulfonic acid chloride, or an isocyanate or vice versa.

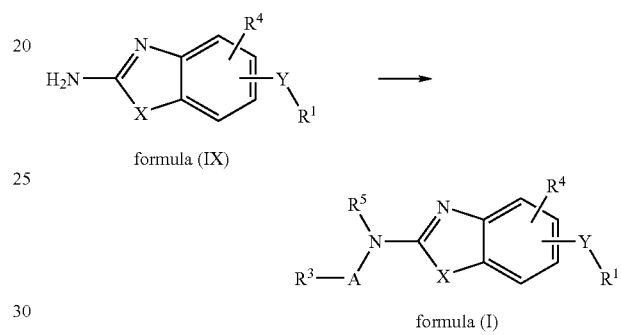

formula (IX)

formula (I)

Compounds of the formula (IX) can be synthesized by reacting a compound of formula (X), wherein R$^4$, X, and Y are as defined above for formula (I), formula (Ia) and formula (II), with a compound of formula (VIII) wherein R$^1$ is as defined above in formula (I), formula (Ia) and formula (II), and LG comprises a leaving group such as Cl, Br, and I. Either nucleophilic substitution or palladium-catalyzed cross-coupling may be applied. Protection (e.g., Boc protection) of the 2-amino group of the benzazole might be necessary. If Y=NR$^2$, R$^2$ may be added before or after addition of R$^1$.

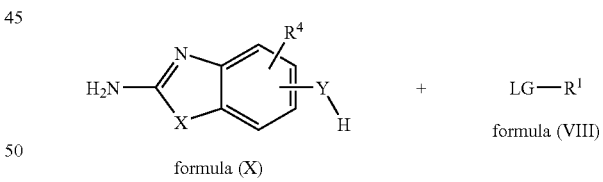

formula (X)    formula (VIII)

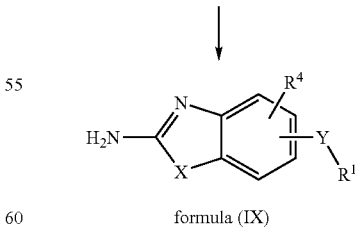

formula (IX)

The compounds of formula (VII), wherein Y=NH, can be synthesized by reduction of a compound of formula (XI), wherein R$^3$, R$^4$, R$^5$, A, and X are as defined above in formula (I), formula (Ia) and formula (II). For example heterogeneous catalytic hydrogenaion may be applied.

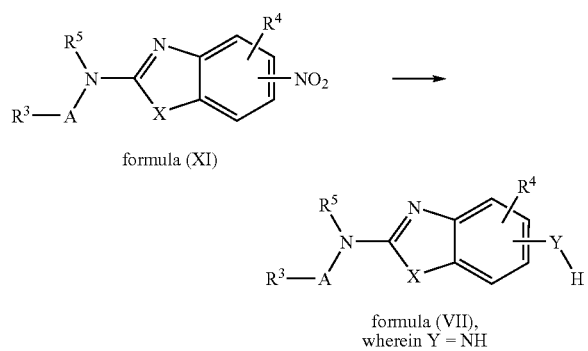

formula (XI)

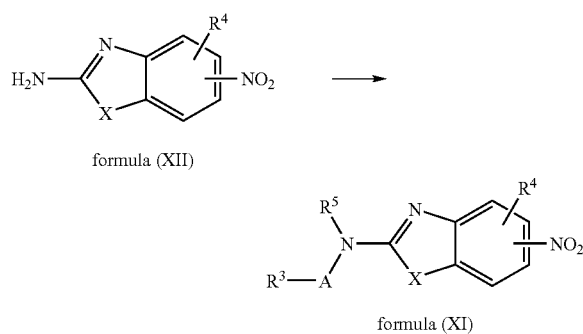

formula (VII),
wherein Y = NH

The compounds of formula (XI) can be synthesized by adding a $R^5$ to a compound of formula (XII), wherein $R^4$ and X are as defined above, followed by reaction with an acid chloride, a carboxylic acid, a sulfonic acid chloride, or an isocyanate or vice versa.

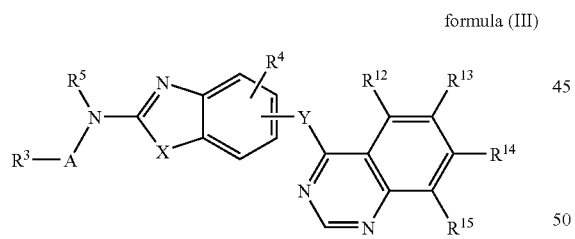

formula (XII)

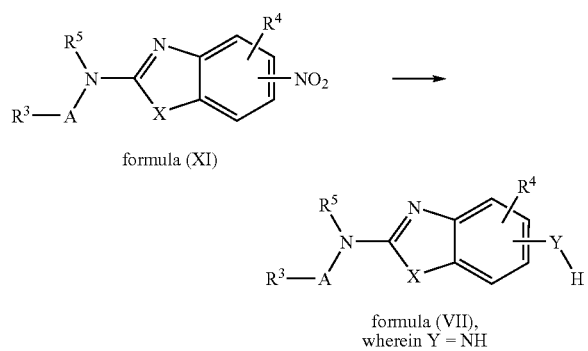

formula (XI)

A preferred embodiment of the invention, are compounds of the formula (III)

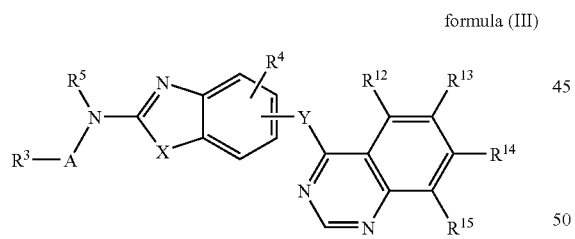

formula (III)

wherein Y is attached at the 5- or 6-position of the benzazole; A, X, Y, $R^3$, $R^4$, $R^5$, $R^{12}$, $R^{13}$, $R^{14}$, $R^{15}$ are as defined above for formula (I).

Another preferred embodiment of the invention, are compounds of formula (III), wherein $R^{12}$ and $R^{15}$ are H and $R^{13}$ and $R^{14}$ independently represent O-alkyl which may be substituted.

A more preferred embodiment of the present invention, are compounds of formula (III), wherein X independently represents S or O; Y represents NH; A independently represents —CO— or ←NHCO—, where ← indicates the point of attachment to $R^3$; $R^3$ is an optionally substituted aryl or heteroaryl group; $R^5$, $R^{12}$ and $R^{15}$ are H; $R^{13}$ and $R^{14}$ are —O-alkyl, which may be substituted.

Another preferred embodiment of the invention, are compounds of the formula (IV)

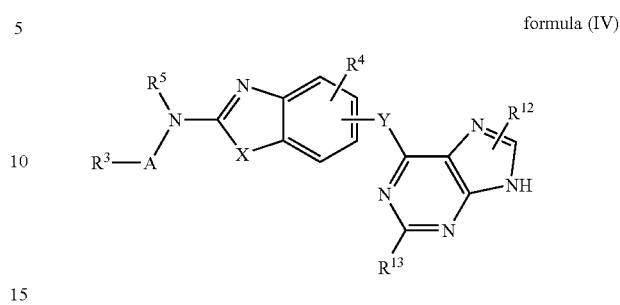

formula (IV)

wherein Y is attached at the 5- or 6-position of the benzazole; A, X, Y, $R^3$, $R^4$, $R^5$, $R^{12}$, $R^{13}$ are as defined above for formula (I).

Another preferred embodiment of the invention are compounds of the formula (V)

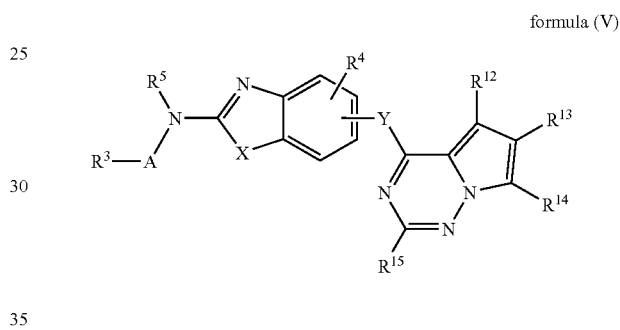

formula (V)

wherein Y is attached at the 5- or 6-position of the benzazole; A, X, Y, $R^3$, $R^4$, $R^5$, $R^{12}$, $R^{13}$, $R^{14}$, $R^{15}$ are as defined above for formula (I).

Another preferred embodiment of the invention, are compounds of the formula (VI)

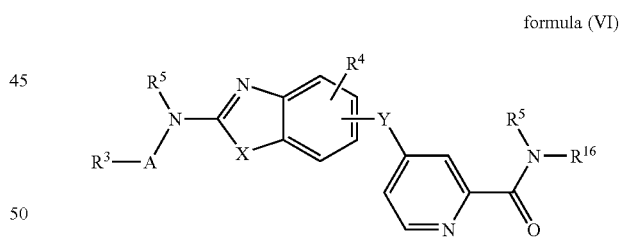

formula (VI)

wherein Y is attached at the 5- or 6-position of the benzazole; A, X, Y, $R^3$, $R^4$, $R^5$, $R^{16}$ are as defined above for formula (I).

Another preferred embodiment of the invention, are compounds of formula (I), where X represents S; Y represents NH; represents —CO—; $R^5$ represents H.

Another preferred embodiment of the invention; are compounds of formula (I), where X represents S; Y represents NH; A represents ←NHCO—, where ← indicates the point of attachment to $R^3$; $R^5$ represents H.

Another preferred embodiment of the invention, are compounds of formula (I), where X represents O; Y represents NH; A represents —CO—; $R^5$ represents H.

Another preferred embodiment of the invention, are compounds of formula (I), where X represents O; Y represents NH; A represents ←NHCO—, where ← indicates the point of attachment to $R^3$; $R^5$ represents H.

Another preferred embodiment of the invention, are compounds of formula (I), are compounds where X represents O; Y represents NH; A represents —CO—; $R^3$ represents an optionally substituted aryl or heteroaryl group; $R^5$ represents H.

A more preferred embodiment of the present invention, are compounds of formula (III), wherein the —Y—$R^1$ substituent is a attached to the 5-position of the benzazole, X independently represents S or O; Y represents NH; A independently represents —CO— or ←NHCO—, where ← indicates the point of attachment to $R^3$, $R^3$ is an optionally substituted aryl or heteroaryl group, $R^5$, $R^{12}$ and $R^{15}$ are H; $R^{13}$ and $R^{14}$ are —O-alkyl, which may be substituted.

A more preferred embodiment of the present invention, are compounds of formula (III), wherein the —Y—$R^1$ substituent is attached to the 6-position of the benzazole, X independently represents S or O; Y represents NH; A independently represents —CO— or ←NHCO—, where ← indicates the point of attachment to $R^3$, $R^3$ is an optionally substituted aryl or heteroaryl group, $R^5$, $R^{12}$ and $R^{15}$ are H; $R^{13}$ and $R^{14}$ are —O-alkyl, which may be substituted.

A more preferred embodiment of the present invention, are compounds of formula (III), wherein the —Y—$R^1$ substituent is attached to the 5-position of the benzazole, X independently represents S or O; Y represents NH; A independently represents —CO— or ←NHCO—, where ← indicates the point of attachment to $R^3$, $R^3$ is an optionally substituted phenyl, $R^5$, $R^{12}$ and $R^{15}$ are H; $R^{13}$ and $R^{14}$ are —O-alkyl, which may be substituted.

A more preferred embodiment of the present invention, are compounds of formula (III), wherein the —Y—$R^1$ substituent is attached to the 6-position of the benzazole, X independently represents S or O; Y represents NH; A independently represents —CO— or ←NHCO—, where ← indicates the point of attachment to $R^3$, $R^3$ is an optionally substituted phenylaryl or heteroaryl group, $R^5$, $R^{12}$ and $R^{15}$ are H; $R^{13}$ and $R^{14}$ are —O-alkyl, which may be substituted.

Another preferred embodiment of the invention, are compounds of formula (I), where $R^3$ is an optionally substituted aryl or heteroaryl group.

Another preferred embodiment of the invention, are compounds of formula (I), where $R^3$ is an optionally substituted phenyl group.

Another preferred embodiment of the invention, are compounds of formula (I), where the —Y—$R^1$ substituent is attached to the 5-position of the benzazole.

Another preferred embodiment of the invention, are compounds of formula (I), where the —Y—$R^1$ substituent is attached to the 6-position of the benzazole.

Another preferred embodiment of the invention, are compounds of formula (III), where $R^3$ is an optionally substituted aryl or heteroaryl group.

Another preferred embodiment of the invention, are compounds of formula (III), where $R^3$ is an optionally substituted phenyl group.

Another preferred embodiment of the invention, are compounds of formula (III), where the —Y—$R^1$ substituent is attached to the 5-position of the benzazole.

Another preferred embodiment of the invention, are compounds of formula (III), where the —Y—$R^1$ substituent is attached to the 6-position of the benzazole.

Another preferred embodiment of the invention, are compounds of formula (III), where X represents S; Y represents NH; A represents —CO—; $R^5$ represents H.

Another preferred embodiment of the invention, are compounds of formula (III), where X represents S; Y represents NH; A represents ←NHCO—, where ← indicates the point of attachment to $R^3$; $R^5$ represents H.

Another preferred embodiment of the invention, are compounds of formula (III), where X represents O; Y represents NH; A represents —CO—; $R^5$ represents H.

Another preferred embodiment of the invention, are compounds of formula (III), where X represents O; Y represents NH; A represents ←NHCO—, where ← indicates the point of attachment to $R^3$; $R^5$ represents H.

Another preferred embodiment of the invention, are compounds of formula (III), are compounds where X represents O; V represents NH; A represents —CO—; $R^3$ represents an optionally substituted aryl or heteroaryl group; $R^5$ represents H.

Another preferred embodiment of the invention, are compounds of formula (Ia), where $X^a$ represents S; $Y^a$ represents NH; $A^a$ represents —CO—; $R^5$ represents H.

Another preferred embodiment of the invention, are compounds of formula (Ia), where $X^a$ represents S; $Y^a$ represents NH; $A^a$ represents ←NHCO—, where ← indicates the point of attachment to $R^3$; $R^5$ represents H.

Another preferred embodiment of the invention, are compounds of formula (Ia), where $R^3$ is an optionally substituted aryl or heteroaryl group.

Another preferred embodiment of the invention, are compounds of formula (Ia), where $R^3$ is an optionally substituted phenyl group.

Another preferred embodiment of the invention, are compounds of formula (Ia), where the —$Y^a$—$R^{1a}$ substituent is attached to the 5-position of the benzazole.

Another preferred embodiment of the invention, are compounds of formula (Ia), where the —$Y^a$—$R^{1a}$ substituent is attached to the 6-position of the benzazole.

Another preferred embodiment of the invention, are compounds of formula (II), where $X^b$ represents S; $Y^b$ represents NH; $A^b$ represents —CO—; $R^5$ represents H.

Another preferred embodiment of the invention, are compounds of formula (II), where $X^b$ represents S; $Y^b$ represents NH; $A^b$ represents ←NHCO—, where ← indicates the point of attachment to $R^3$; $R^5$ represents H.

Another preferred embodiment of the invention, are compounds of formula (II), where $R^3$ is an optionally substituted aryl or heteroaryl group.

Another preferred embodiment of the invention, are compounds of formula (II), where $R^3$ is an optionally substituted phenyl group.

Another preferred embodiment of the invention, are compounds of formula (II), where the —$Y^b$— substituent is attached to the 5-position of the benzazole.

Another preferred embodiment of the invention, are compounds of formula (II), where the —$Y^b$— substituent is attached to the 6-position of the benzazole.

Another preferred embodiment are compositions containing one ore more compounds of the present invention and a pharmaceutical acceptable carrier or diluent The compounds of the present invention can form salts with inorganic or organic acids or bases. Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluenesulfonic acid and others.

Salts of phosphonoxy- and phosphonoxyalkyl groups may be those formed with alkali metal ions e.g. sodium or potassium, or those formed with alkaline earth metal ions e.g. calcium or magnesium, or those formed with zinc ions.

Such salts of the compounds of the present invention may be anhydrous or solvated. Such salts can be produced by methods known to someone of skill in the art and described in the prior art.

Other salts like oxalate derived from oxalic acid, which is not considered as pharmaceutically acceptable can be appropriate as intermediates for the production of compounds of the present invention or a pharmaceutically acceptable salt thereof or physiologically functional derivative, or a stereoisomer thereof.

The compounds according to the invention and medicaments prepared therewith are generally useful for the treatment of cell proliferation disorders, for the treatment or prophylaxis of immunological diseases and conditions (as for instance inflammatory diseases, neuroimmunological diseases, autoimmune diseases or other).

The compounds of the present invention are useful for the treatment of diseases which are caused by malignant cell proliferation, such as all forms of solid tumors, leukemias and lymphomas. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, myeloma), or lymphomas (e.g. Hodgkin's and non-Hodgkin's lymphomas), or solid tumors (for example breast, prostate, liver, bladder, lung, esophageal, stomach, colorectal, genitourinary, gastrointestinal, skin, pancreatic, brain, uterine, colon, head and neck, and ovarian, melanoma, astrocytoma, small cell lung cancer, glioma, basal and squameous cell carcinoma, sarcomas as Kaposi's sarcoma and osteosarcoma).

Other aspects of the present invention relate to benzazole derivatives as new pharmaceutically active agents, especially for the preparation of a pharmaceutical composition for the treatment of diseases which are cured or relieved by the inhibition of one or several kinases and/or phosphatases.

In another more preferred embodiment of the invention the compounds of the present invention may be used for treating and/or preventing diseases by inhibition of one ore more kinases like: Aurora A, Aurora B, EGF-R, ERBB2, IGF1-R, PDGFR, FLT3 VEGF-R2, VEGF-R3, EPHB4, Tie2, FAK and SRC.

The compounds according to the present invention or a pharmaceutically acceptable salt or physiologically functional derivative or a stereoisomer thereof if desired with appropriate adjuvants and additives for the production of a medicament for the treatment or prevention of a disease characterized by hyperproliferation of keratinocytes and/or T cells, especially inflammatory disorders and immune disorders, preferably selected from the group consisting of Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Leishmania, and immunesuppressed disease states such as viral infections following allograft transplantations, AIDS, cancer, chronic active hepatitis diabetes, toxic chock syndrome and food poisoning.

"Treatment" according to the present invention is intended to mean complete or partial healing of a disease, prevention of a disease, or alleviation of a disease or stop of progression of a given disease.

The compounds of the present invention can further be used for diseases that are caused by protozoal infestations in humans and animals.

The compounds of the present invention can further be used for viral infections or other infections caused for instance by *Pneumocystis carinii*.

Furthermore, the invention relates to a method of treatment or prevention of diseases which comprises the administration of an effective amount of compounds of the formula (I) or a pharmaceuticauly acceptable salt or physiologically functional derivative or a stereoisomer thereof.

The compounds of the according invention, and their pharmacologically acceptable salts can be administered to animals, preferably to mammals, and in particular to humans, as therapeutics per se, as mixtures with one another or in the form of pharmaceutical preparations which allow enteral or parental use and which as active constituent contain an effective dose of at least one compound of the present invention or a salt thereof, in addition to customary pharmaceutically innocuous excipients and additives.

The production of medicaments containing the compounds according to the present invention and their application can be performed according to well-known pharmaceutical methods.

While the compounds according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds may be anhydrous or solvated.

In a preferred embodiment, the invention provides medicaments comprising compounds according to the present invention, or a pharmaceutically acceptable salt or physiologically functional derivative or a stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraaterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

For preparing a medicament from a compounds of the present invention and pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use be prepared -by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In an especially preferred embodiment of the present invention the medicament is applied topically. This reduces possible side effects and limits the necessary treatment to those areas affected.

Preferably the medicament is prepared in form of an ointment, a gel, a plaster, an emulsion, a lotion, a foam, a cream of mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth;

pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Pharmaceutical compositions can also contain two or more compounds of the present invention or their pharmacologically acceptable salts and also other therapeutically active substances.

Thus, the compounds of the present invention can be used in the form of one compound alone or in combination with other active compounds—for example with medicaments already known for the treatment of the aforementioned diseases, whereby in the latter case a favorable additive, amplifying effect is noticed.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice. However, those of skill in the art should, in light of the present disclosure, appreciate that many changes can be made in the specific embodiments that are disclosed without departing from the spirit and scope of the invention as set out in the appended claims. All references cited are incorporated herein by reference.

EXAMPLES

Abbreviations, min. minute(s); h, hour(s), r.t., room temperature; $R_t$, retention time; $\Psi$, pseudo; s, singlet; t, triplet, quint, quintet; br., broad; J, coupling constant; pTLC, preparative thin layer chromatography; DMAP, 4-dimethylaminopyridine, IM, Intermediate.

NMR spectra: Bruker Avance 300 Mz. The $^1$H NMR spectra were recorded at 300 MHz using the residual solvent peak as internal standard ($CDCl_3$, $\delta_H$=7.26).

Analytical LC/ESI-MS: 2× Waters 600 Multisolvent Delivery System. 50 µl Sample loop. Column, Chromolith Speed ROD RP18e (Merck, Darmstadt), 50×4.6 mm, with 2 µm prefilter (Merck). Eluent A, $H_2O$+0.1% $HCO_2H$; eluent B, MeCN. Gradient, 5% B to 100% B within 5 min; flow, 3 ml/min. Waers LCZ single quadrupol mass spectrometer with electrospray source. MS method, Ms8minPM-80-800-20V; positive/negative ion mode scantung, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

Preparative HPLC-MS. Waters 600 Multisolvent Delivery System with peparative pump heads. 2000 µl or 5000 µl Sample loop. Column, Waters X-Terra RP18, 7 µm, 19×150 mm with X-Terra RP18 guard cartridge 7 µm, 19×10 mm; used at flow rate 20 ml/min or YMC ODS-A, 120 Å, 40×150 mm with X-Terra RP18 guard cartridge 7 µm, 19×10 mm; used at flow rate 50 ml/min. Make-up solvent: MeCN—H—HCO7H 80:20:0.05 (v:v:v). Eluent A, $H_2O$+0.1% $HCO_2H$; vlucat B, MeCN. Different linear gradients from 5-100% eluent B, adapted to sample. Injection volume: 500 µl-2000 µl depending on sample. Waters ZQ single quadrupol mass spectrometer with electrospray source. Positive or negative ion mode scanning m/z 80-800 in 1 s; capillary, 3.5 kV or 3.0 kV; cone voltage, 20 V; multiplier voltage, 400 V; probe and desolvation gas temperature, 120° C. and 350° C., respectively. Waters Fraction Collector II with mass-triggered fraction collection. Waters 996 photo diode array detector.

Syntheses of Intermediates

Intermediate 1

N-(6-Aminobenzoxazol-2-yl)benzamide

Step 1. A solution of cyanogen bromide (3.50 g, 33 mmol; caution: highly toxic! Waste disposal: addition of excess NaOCl to a basic aqueous solution of cyanogen bromide) in tetrahydrofuran (3 mL) was added to a solution of 2-amino-5-nitrophenol (4.62 g, 30 mmol) in tetrahydrofuran (20 mL). After stirring for 1 day at r.t, a precipitate had formed which was dissolved by addition of water (5 mL). After stirring further 3 days at r.t., water (10 mL) was added and NaOH was added until the mixture turned basic. The tetrahydrofuran was removed in vacuo and the precipitate formed in the remaining aqueous phase was separated by filtration, washed with water and recrystallized from methanol (100 mL). Upon additional fractional crystallisation of the mother liquor, a total of 3.80 g (21.2 mmol, 71%) of 2-amino-6-nitrobenzoxazole was obtained as a brown solid. LC/ESI-MS: m/z=180 [M+H]$^+$; m/z=178 [M]–H$^-$; R=2.52 min.

Step 2. Benzoyl chloride (1.17 mL, 10.0 mmol) was added to a suspension of 2-amino-6-nitrobenzoxazole (1.50 g, 8.37 mmol) in pyrdine (10 mL). After stirring for 24 h at 80° C., the solution was poured into water (250 mL). The mixture was stirred overnight at r.t. and the resulting precipitate was separated by filtration. N-(6-Nitrobenzoxazol-2-yl)benzamide (2.08 g, 7.32 mmol, 88%) was thus obtained as a yellow solid. LC/ESI-MS: /z =284 [M+H]$^+$; m/z=282 [M–H]$^-$; R$_f$=3.13 min.

Step 3. To a solution of N-(6-nitrobenzoxazol-2-yl)benzamide (2.03 g, 7.17 mmol) in dimethylformamide (60 mL), palladium on charcoal (1.52 g, 10% Pd, 1.43 mmol Pd) was added and the air was replaced with hydrogen (1 bar). The mixture was stirred for 2 h at 60° C. and then overnight at r.t. The palladium was removed by filtration through a pad of celite. After concentration to 20 mL, water was added and the resulting precipitate was separated by filtration to obtain N-(6-aminobenzoxazol-2-yl)benzamide (0.823 g, 3.25 mmol, 45%) as a brown solid. LC/ESI-MS: m/z=254 [M+H]$^+$; m/z=252 [M–H]$^-$; R$_f$=1.92 min.

Intermediate 2

N-(6-Aminobenzothiazol-2-yl)benzamide

Step 1. To a suspension of 2-amino-6-nitrobenzothiazole (Sigma Aldrich, 2.93 g, 15 mmol) in pyridine (20 mL), benzoyl chloride (1.74 mL, 15 mmol) was added. After stirring over-night at r.t., additional benzoyl chloride (1.74 mL, 15 mmol) was added and the mixture was stirred at 60° C. After completion of the reaction, the mixture was poured into water (250 mL) and stirred overnight at r.t. Separation of the resulting precipitate yielded N-6-nitrobenzotihiazol-2-yl)benzamide (3.87 g, 12.9 mmol, 86%) as a yellow solid. LC/ESI-MS: m/z=300 [M+H]$^+$; m/z=298 [M–H]$^-$; R$_f$=3.93 min.

Step 2. A mixture of N-(6-nitrobenzothiazol-2-yl)benzamide (3.77 g, 12.6 mmol), palladium on charcoal (2 g, 10% Pd, 1.88 mmol Pd), dimethyl formamide (80 mL) and ethyl acetate (20 mL) was hydrogenated (1 bar) for 2 h at 60° C. The palladium was removed by filtration through a pad of celite. After concentration to 20 mL, water was added and the resulting precipitate was separated by filtration to obtain N-(6-aminobenzothiazol-2-yl)-benzamide (3.15 g, 11.7 mmol, 93%) as a grey solid. LC/ESI-MS: m/z=270 [M+H]$^+$; m/z=268 [M–H]$^-$; R$_f$=2.27 min.

Intermediate 3

N-(6-Aminobenzothiazol-2-yl)isonicotinamide

Step 1. To a mixture of 2-amino-6-nitrobenzothiazole (Sigma Aldrich, 1.95 g, 10 mmol) and pyridine (40 mL), benzoyl chloride (2.1 mL, 18 mmol) was added. After stirring for 5 h at 80° C., water (10 mL) was added. The mixture was stirred for 0.5 h at r.t., then methanol (30 mL) and water (50 mL) were added. The precipitated N-(6-nitrobenzothiazol-2-yl)-isonicotinamide was separated by filtration. The crude product was taken up in dimethylformamide and precipitated again by addition of methanol and water (2.53 g, 8.42 mmol, 84%). LC/ESI-MS: m/z=301 [M+H]$^+$; m/z=299 [M–H]$^-$; R$_f$=3.48 min.

Step 2. N-(6-Nitrobenzothiazol-2-yl)isonicotinamide (2.42 g, 8.04 mmol) was suspended in ethyl acetate (150 mL), and dimethylformamide was added until dissolution occured. After addition of palladium on charcoal (4.25 g, 10% Pd, 4 mmol Pd) the mixtue was hydrogenated (1 bar) at 60° C. until completion of the reaction. The palladium was removed by filtration through a pad of celite and the solvent was evaporated. The residue was taken up in little methanol and precipitated by addition of water to obtain N-(6-aminobenzothiazol-2-yl)isonicotinamide (1.73 g, 6.4 mmol, 80%). LC/ESI-MS: m/z=271 [M+H]$^+$; m/z=269 [M–H]$^-$; R$_f$=1.43 min.

Intermediate 4

N-(6-Aminobenzothiazol-2-yl)nicotinamide

Step 1. A mixture of 2-amino-6-nitrobenzothiazole (0.976 g, 5 mmol), nicotinoyl chloride hydrochloride (1.07 g, 6 mmol), triethylamine (1.9 ml, 13.8 mmol), DMAP (catalytic amount) and dioxane (50 mL) was heated to reflux for 7 h. After addition of nicotinoyl chloride hydrochloride (0.89 g, 5 mmol) and triethylamine (1.8 mL, 12.5 mmol), heating was continued for 5 h. After cooling to r.t., the precipitate was separated by filtration. The solid was treated with boiling methanol (25 mL) to remove soluble impurities. There was thus obtained N-(6-nitrobenzothiazol-2-yl)nicotinamide (1.36 g, 4.53 mmol, 91%). LC/ESI-MS: m/z=301 [M+H]$^+$; m/z=299 [M–H]$^-$; R$_f$=3.54 min.

Step 2. N-(6-Nitrobenzothiazol-2-yl)nicotinamide (0.50 g, 1.67 mmol) was dissolved in dimethylsulfoxide (50 mL) by warming. After addition of palladium on charcoal (0.089 g, 10% Pd, 0.08 mmol Pd), the rntrre ,shydrogened for 5.5 h at 80° C. The palladium was removed by hot filtration through a pad of silica. After removal of the solvent, N-(6-aminobenzothiazol-2-yl)nicotinamide (0145 g, 1.67 mmol, 100%) was obtained as a brownish solid. LC/ESI-MS: m/z=271 [M+H]$^+$; m/z=269 [M–H]$^-$; R$_f$=1.67 min.

Intermediate 5

N-(5-Aminobenzothiazol-2-yl)benzamide

Step 1. Ammonium thiocyanate (8.55 g, 112.5 mmol) was dissolved in acetone (80 mL) and acetyl chloride (8.83 g, 112.5 mmol) was added dropwise. After stirring for 1 h at r.t., the solid was filtered off, and the filtrate was added to a solution of 2-fluoro-5-nitroaniline in acetone (45 mL). The mixture was refluxed for 6 h, then the solution was concentrated and stored overnight at r.t. The precipitated, 1-acetyl-3-2-fluoro-5-nitrophenyl)thiourea was filtered off, washed with acetone and dried. The mother liquor was concentrated and recrystallized from acetone to yield another batch of the product. A total of 12.55 g (48.8 mmol, 43%) of a grey solid a obtainedi LC/ESI-MS: m/z=258 [M+H]$^+$; R$_t$=3.42 min.

Step 2. A solution of 1-acetyl-3-(2-fluoro-5-nitrophenyl)thiourea (9.63 g, 37.4 mmol) in methanol (400 mL) was quickly poured into a solution of sodium methanolate (concentration, 0.5 mol/L) in methanol (100 mL). The solution was stored overnight without stirring. The precipitated 2-amino-5-nitrobenzothiazole was filtered off, washed with methanol and dried (yellow crystals, 6.87 g, 35.2 mmol, 94%). LC/ESI-MS: m/z=196 [M+H]$^+$; m/z=194 [M−H]$^−$; R$_t$=2.71 min.

Step 3. A mixture of 2-amino-5-nitrobenzothiazole (1.52 g, 7.8 mmol), benzoyl chloride (1.36 mL, 11.7 mmol) and pyridine (15 mL) was heated to 60° C. for 24 h. The mixture was poured into water (250 mL), and the resulting precipitate was separated by filtration to yield N-(5-nitrobenzothiazol-2-yl)benzamide (1:83 g, 6.12 mmol, 78%) as a yellow solid.

Step 4. A mixture of N-(5-nitrobenzothiazol-2-yl)benzamide (1.79 g, 6.00 mmol) and palladium on charcoal (0.95 g, 10% Pd, 0.9 mmol Pd) in dimethylfonmamide (40 mL) was hydrogenated (1 bar) for 2 h at 100° C. The palladium was removed by filtration through a pad of celite and the filtrate was concentrated to a small volume. Upon addition of water (200 mL), a precipitate formed which was separated by filtration. There was thus obtained N-(5-aminobenzothiazol-2-yl)benzamide (1.39 g, 5.14 mmol, 86%) as a grey solid. LC/ESI-MS: m/z=300 [M+H]$^+$; m/z=298 [M−H]$^−$; R$_t$=4.2 min.

Intermediate 7

4-Chloro-6-methoxy-7-[3-(4-methylpiperazin-1-yl)propoxy]quinazoline

Step 1. To a solution of methyl vanillate (7.29 g, 40 mmol) in dimethylformamide (25 mL), potassium carbonate (8.29 g, 60 mmol) and benzyl bromide (5.26 mL, 44 mmol) were added. The mixture was heated to 100° C. for 3 h. After cooling to r.t., water was added and the product was extracted several times with ethyl acetate. The combined organic phases were washed with water and brine. After drying over Na$_2$SO$_4$, the solvent was removed to yield methyl 4-benzyloxy-3-methoxybenzoate (10.8 g, 39.7 mmol, 99%) as a grey solid which was used without further purification. LC/ESI-MS: m/z=273 [M+H]$^+$; R$_t$=3.82 min.

Step 2. Methyl 4-benzyloxy-3-methoxybenzoate (10.9 g, 40.0 mmol) was converted into methyl 4-benzyloxy-5-methoxy-2-nitrobenzoate (11.6 g, 36.6 mmol, 91%) as described in US 02/0026052 A1, page 51, referent example 15. LC/ESI-MS: m/z=318 [M+H]$^+$; R$_t$=3.85 min.

Step 3. In a 1 l Schlenk flask filled with argon, methyl 4benzyloxy-5-methoxy-2-nitrobenzoate (11.60 g, 36.6 mmol) and palladium on charcoal (1.17 g, 10% Pd, 1.1 mmol Pd) were combined and tetrahydrofuran (250 mL) was added. The argon was replaced with hydrogen (1 bar), and the mixture was vigorously stirred at r.t. until completion of the reaction. The palladium was separated by filtration through a pad of celite and the solvent was removed to obtain methyl 2-amino-4-hydroxy-5-methoxybenzoate (6.56 g, 36.0 mmol, 98%) which was used without further purification LC/ESI-MS: m/z=166 [M−CH$_4$O+H]$^+$; R$_t$=2.17 min.

Step 4. A mixture of formamide (29 mL), ammonium formate (3.41 g, 54 mmol) and methyl 2-amino-4-hydroxy-5-methoxybenzoate (6.56 g, 36.0 mmol) was heated to 140° C. for 4 h. After cooling to r.t., water (75 mL) was added. After stirring for 1 h, the precipitated 7-hydroxy-6-methoxy-3,4-dihydroquinazolin-4-one was filtered off, washed with water and dried (grey solid, 5.86 g, 30.5 mmol, 85%). LC/ESI-MS: m/z=193 [M+H]$^+$; m/z=191 [M−H]$^−$; R$_t$=1.53 min.

Step 5. A mixture of 7-hydroxy-6-ethoxy-3,4-dihydroquinazolin-4-one (5.86 g, 30.5 mmol) and acetic anhydride (21.5 mL, 229 mmol) in pyridine (4.9 mL, 61 mmol) was heated to 100° C. for 4 h. After cooling to r.t., ice water (200 mL) was added and the mixture was vigorously stirred for 1 h. The precipitated 7-acetoxy-6-methoxy-3,4-dihydroquinazolin-4-one was filtered off, washed with water and dried (grey solid, 6.64 g, 28.3 mmol, 93%). LC/ESI-MS: m/z=235 [M+H]$^+$; m/z=233 [M−H]$^−$; R$_t$=2.88 min. Cf. also WO 04/043472, page 32.

Step 6. 7-Acetoxy-6-methoxy-3,4-dihydroquinazolin-4one (2.34 , 10.0 mmol) was converted into 4-chloro-7-hydroxy-6-methoxyquinazoline (1.22 g, 5.79 mmol, 58%) as described in WO 04/043472, page 32. LC/ESI-MS: m/z=211 [M($^{35}$Cl)+H]$^+$; m/z=209 [M($^{35}$Cl)−H]$^−$; R$_t$=2.45 min.

Step 7. Di-tert-butyl azodicarboxylate (0.478 g, 2.08 mmol) was added portionwise to a mixture of 4-chloro-7-hydroxy-6-methoxyquinazoline (0.350 g, 1.66 mmol), 3-(4-methyl-piperazin-1-yl)-propan-1-ol (Intermediate 9, 0.276 g, 1.74 mmol), and triphenylphosphine (0.544 g, 2.08 mmol) in dichloromethane (20 mL) at r.t. If necessary, further alcohol was added. After stirring for 2 h, the solution was concentrated to 10 mL, mounted on silica and chromatographed (gradient, dichloromethane to dichloromethane:methol=3.2 within 1 h) to obtain 4-chloro-6-methoxy-7-[3-(4-methylpiperazin-1-yl)propoxy]quinazoline (brownish solid, 0.431 g, 1.23 mmol, 74%). LC/ESI-MS: m/z=351 [M($^{35}$Cl)+H]$^+$; R$_t$=1.88 min Cf. also WO 04/143472, page 32, Intermediate 8

4-Chloro-7-methoxy-6-[3-(4-methylpiperazin-1-yl)propoxy]quinazoline

Step 1. Methyl isovanillate (2.73 g, 15 mmol) was converted into methyl 3-benzyloxy-4-methoxybenzoate (3.91 g, 14.4 mmol, 96%) in analogy to the preparation of Intermediate 7, Step 1. LC/ESI-MS: m/z=273 [M+H]$^+$; R$_t$=3.90 min.

Step 2. Methyl 3-benzyloxy-4-methoxybenzoate (2.83 g, 10.4 mmol) was converted into methyl 5-benzyloxy-4-methoxy-2-nitrobenzoate (3.08 g, 9.71 mmol, 94%) in analogy to the preparation of Intermediate 7, Step 2. LC/ESI-MS: m/z=318 [M+H]$^+$; R$_t$=4.00 min.

Step 3. Methyl 5-benzyloxy-4-methoxy-2-nitrobenzoate (4.11 g, 13.0 mmol) was converted into methyl 2-amino-5-hydroxy-4-methoxybenzoate (2.56 g, 13.0 mmol, 100%) in analogy to the preparation of Intermediate 7, Step 3. LC/ESI-MS: m/z=166 [M−CH$_4$O+H]$^+$; R$_t$=1.95 min.

Step 4. 2-Amino-5-hydroxy-4-methoxybenzoate (2.56 g, 13.0 mmol) was converted into 6-hydroxy-7-methoxy-3,4-dihydroquinazolin-4-one (1.91 g, 9.94 mmol 76%) in analogy to the preparation of Intermediate 7, Step 4. LC/ESI-MS: m/z=193 [M+H]$^+$; m/z=191 [M−H]$^−$; R$_t$=1.77 min.

Step 5. 6Hydroxy-7-methoxy-3,4-dihydroquinazolin-4-one (1.90 g, 9.86 mmol) was converted into 6-acetoxy-7-methoxy-3,4-dihydroquinazolin-4-one (2.22 g, 9.48 mmol, 96%) in analogy to the preparation of Intermediate 7, Step 5.

LC/ESI-MS; m/z=235 [M+H]⁺; m/z=233 [M−H]⁻, R_f=2.20 min.

Step 6. 6-Acetoxy-7-methoxy-3,4-dihydroquinazolin-4-one (0.468 g, 2.00 mmol) was converted into 4-chloro-6-hydroxy-7-methoxyquinazoline (0.398 g, 1.89 mmol, 95%) in analogy to the preparation of Intermediate 7, Step 6. LC/ESI-MS: m/z=211 [M($^{35}$Cl)+H]⁺; m/z=209 [M($^{35}$Cl)−H]⁻; R_f=2.40 min.

Step 7. 4-Chloro-6-hydroxy-7-methoxyquinazoline (0.373 g, 1.77 mmol) was converted into 4-chloro-7-methoxy-6-[3-4-methylpiperazin-1-yl)propoxy]quinazoline (0.451 g, 1.29 mmol, 73%) in analogy to the preparation of Intermediate 7, Step 7. LC/ESI-MS: m/z=351 [M($^{35}$Cl)+H]⁺; R_f=1.82 min.

Intermediate 9

3-(4-Methylpiperazin-1-yl)-propan-1-ol

1-Methylpiperazine (6.99 mL, 63 mol) was dissolved in toluene (30 mL). 3-Bromopropanol (2.62 mL, 30 mmol) was slowly and the mixture was stirred overnight at r.t. After heating to 80° C. for 2 h and cooling to r.t., the mixture was filtered and the filter cake was thoroughly washed with toluene. After removal of the solvent, the residue was subjected to distillation (b.p., 180° C./2 mbar) to obtain a colourless oil (4.08 g, 25.8 mmol, 86%). ¹H NNR (CDCl₃): δ=1.70 (Ψ-quint, J≈5.8 Hz, 2 H), 2.26 (s, 3 H), 2.35-2.6 (m, 8 H), 2.60 (Ψ-t, J=5.8 Hz, 2 H), 3.77 (Ψ-t, J=5.3 Hz, 2 H), 4.09 (s, br., 1 H).

Intermediate 10

2-Chloro-4-(4-methylpiperazin1-yl)pyrimidine

A mixture of 2,4-dichloropyrimidine (0.967 g, 6.49 mmol), 1-methylpiperazine (0.65 g, 6.40 mmol), and ethyldiisopropylamine (2.8 mL, 16.22 mmol) in ethanol (13 mL) was stirred at −10° C. for 2 h and then at r.t. overnight. The mixture was partitioned between H₂O/brine (3:1; 100 mL) and chloroform (3×70 mL). The combined organic phases were washed once with brine (50 mL) an dried over MgSO₄. Removal of solvent yielded a pale-beige solid, which was washed with ethyl acetate/ultrasound to give the desired product as a colourless powder, which was further washed with Et₂O. Additional product was obtained upon fractional crystallization of the washing solution. A total of 0.741 g (3.48 mmol, 54%) of 2-chloro-4-(4-methylpiperazin1-yl)pyrimidine was obtained. LC/ESI-MS: m/z=213 [M($^{35}$Cl)+H]⁺; R_f=0.5 min.

Intermediate 11

(2-Chloropyrimidin-4-yl)-(5-methylpyrazol-3-yl)amine

A mixture of 2,4-dichloropyrimidine (0.967 g, 6.49 mmol), 3-amino-5-methylpyrazole (0.63 g, 6.40 mmol), and ethyldiisopropylamine (2.8 mL, 16.22 mmol) in ethanol (13 mL) was stirred at −10° C. for 2 h, then at r.t. overnight, and finally at 50° C. for 3.5 h. The mixture was concentrated to a total volume of approximately 10 mL. Upon repeated addition of diethylether, (2-chloropyrimidin-4-yl)-(5-methylpyrazol-3-yl)amine (0.258 g, 1.23 mmol, 19%) was obtained as colourless crystals. LC/ESI-MS: m/z=210 [M($^{35}$Cl)+H]⁺; m/z=208 [M($^{35}$Cl)−H]⁻; R_f=230 min.

Intermediate 12

N⁶-{6-Methoxy-7-[3-(4-methyl-piperazin-1-yl)-propoxy]-quinazolin-4yl}-benzothiazole-2,6-diamine hydrochloride Intermediate 7 (0.285 mmol) and benzothiazole-2,6-diamine (47 mg, 0.285 mmol) were dissolved in butanol (5 mL). HCl in dioxane (0.214 mL, 4 M solution) was added. The reaction was finished after 6 h at 100° C. The resulting precipitate was filtered, washed with dichloromethane, and dried in vacuo, (97% yield). LC/ESI-MS: m/z=480 [M+H]⁺.

Intermediate 13

N⁵-{6-Methoxy-7-[3-(4-methyl-piperazin-1-yl)-propoxy]-quinazolin-4-yl}-benzothiazole-2,5-amine hydrochloride Intermediate 7 (0.285 mmol) and benzothiazole-2,5-diamine (47 mg, 0.285 mmol) were dissolved in butanol (5 mL). HCl in dioxane (0.214 mL, 4 M solution) was added. The reaction was finished after 6 h at 100° C. The resulting precipitate was filtered, washed with dichloromethane, and dried in vacuo (97% yield). LC/ESI-MS: m/z=480 [M+H]⁺.

Intermediate 14

1-[6-(6-Chloro-pyrimidin-4-ylamino)-benzothiazol-2-yl]-3-(2-methoxy-5-methyl-phenyl)-urea A mixture of 4,6-dichloropyrimidine (180 mg, 1.21 mmol), benzothiazole-2,6-diamine (200 mg, 1.21 mmol), sodium iodide (216 mg, 1.45 mmol), ethyl diisopropylamine (0.25 mL, 1.45 mmol) and DMF (10 mL) was heated at 85° C. for 3 h. 2-Methoxy-5-methylphenyl isocyanate (0.20 mL, 1.33 mmol) was added and heating was continued at 85° C. for 3 h. The solvent was removed and the residue treated with CH₂Cl₂. The precipitate was separated (0.57 g, 85%). LC/ESI-MS: m/z=441 [M+H]⁺; m/z=439 [M−H]⁻; R_f=3.64 min.

Syntheses of the Examples

Example 1

N-[6-(6,7-Dimethoxyquinazolin-4-ylamino)benzoxazol-2-yl]benzamide was prepared by heating a mixture of N-(6-aminobenzoxazol-2-yl)benzamide (IM 1, 30 mg, 0.118 mmol) and 4-chloro-6,7-dimethoxyquinazoline (Fluorochem, 26.5 mg, 0.118 mmol) in ethanol (3 mL) to 80° C. for 2 h. The resulting precipitate was separated by filtration, washed with ethanol and dried (yellow solid, 38 mg, 85 µmol, 72%). LC/ESI-MS: m/z=442 [M+H]⁺; m/z=440 [M−H]⁻; R_f=2.43 min.

Example 2

N-[6-6,7-Dimethoxyquinazolin-4-ylamino)benzothiazol-2-yl]benzamide was prepared by heating a mixture of N-(6-aminobenzothiazol-2-yl)benzamide (IM 2, 30 mg, 0.111 mmol) and 4-chloro-6,7-dimethoxyquinazoline (Fluorochem, 25 mg, 0.111 mmol) in ethylene glycol (0.7 mL) to 100° C. for 2 h. Brine (25 mL) and saturated sodium hydrogencarbonate solution (25 mL) were added and the product was extracted with chloroform (3×40 mL). After drying out Na₂SO₄, the solvent was removed and the residue was purified by pTLC (petroleum ether:dichloromethane:methanol=12:14:3) to yield a yellow solid (19 mg, 41 μmol, 37%). LC/ESI-MS: m/z 458 [M+H]$^+$; m/z=456 [M−H]$^−$; R$_t$=2.88 min.

Example 3

N-[6-(6,7-Dimethoxyquinazolin-4-ylamino)benzothiazol-2-yl]isonicotinamide was prepared by heating a mixture of N-(6-aminobenzothiazol-2-yl)isonicotinamide Intermediate 3, 50 mg, 0.185 mmol) and 4-chloro-6,7-dimethoxyquinazoline (Fluorochem, 42 mg, 0.185 mmol in ethanol (3 mL) to 80° C. for 2 h. The resulting precipitate was separated by filtration, washed with ethanol and dried (yellow solid, 82 mg, 0.179 mmol, 97%). LC/ESI-MS: m/z 459 [M+H]$^+$; m/z=457 [M−H]$^−$; R$_t$=2.65 min.

Example 4

N-[6-(6,7-Dimethoxyquinazolin-4-ylamino)benzothiazol-2-yl]nicotinamide was prepared by heating a mixture of N-(6-aminobenzothiazol-2-yl)nicotinamide (IM 4, 30 mg, 0.111 mmol) and 4-chloro-6,7-dimethoxyquinazoline (Fluorochem, 25 mg, 0.111 mmol) in ethanol (3 mL) to 80° C. for 2 h. The resulting precipitate was separated by filtration, washed with ethanol and dried (yellow solid, 44 mg, 96 μmol, 87%), LC/ESI-MS: m/z=459 [M+H]$^+$; m/z=457 [M+H]$^−$; R$_t$=2.60 min.

Example 5

N-(6-{6-Methoxy-7-[3-(4-methylpiperazin-1-yl)propoxy]quinazolin-4-yl-amino}benzothiazol-2-yl)benzamide was prepared by heating a mixture of N-6-amino-benzothiazol-2-yl)benzamide (IM 2, 30 mg, 0.111 mmol), 4-chloro-6-methoxy-7-[3-4-methylpiperazin-1 yl)propoxy]quinazoline (Intermediate 7, 39 mg, 0.111 mmol), ethyldiisopropylamine (40 μL, 0.2221 mmol), and HCl (84 μL, 4 M solution in dioxane, 0.333 mmol) in n-butanol (3 mL) to 110° C. for 2 h. Saturated sodium hydrogencarbonate solution was added and the product was extracted with chloroform. After washing with water and drying over Na$_2$SO$_4$, the solvent was removed. The residue was taken up in little methanol, then water was slowly added. After stirring the mixture overnight, a brownish solid was obtained (38 mg, 65 μmol, 59%). LC/ESI-MS: m/z=584 [M+H]$^+$; m/z=582 [M−H]$^−$; R$_t$=2.27 min.

Example 6

N-(6-{7-Methoxy-6-[3-(4-methylpiperazin-1-yl)propoxy]quinazolin-4yl-amino}benzothiazol-2-yl)benzamide was prepared by heating a mixture of N-(6-amino-benzothiazol-2-yl)benzamide (Intermediate 2, 40 mg. 0.148 μmol), 4-chloro-7-methoxy-6-[3-(4methylpiperazin-1-yl)propoxy] quinazoline (IM 8, 52 mg, 0.148 mmol), and HCl (112 μL, 4 M solution in dioxane, 0.444 mmol) in n-butanol (6 mL) to 110° C. for 5 h. Saturated sodium hydrogencarbonate solution was added and the product was extracted with ethyl acetate. After washing with water and drying over Na$_2$SO$_4$, the solvent was removed. The residue was taken up in little methanol, then water was slowly added. After stirring the mixture overnight, a grey solid was obtained (39 mg, 66 μmol, 45%). LC(ESI-MS: m/z=584 [M+H]$^+$; m/z=582 [M−H]$^−$; R$_t$=2.26 min.

Example 7

N-[6-(Purin-6-ylamino)benzothiazol-2-yl]benzamide was prepared by heating a mixture of N-(6-aminobenzothiazol-2-yl)benzamide (IM 2, 50 mg, 0.186 mmol) and 6-chloropurine (29 mg, 0.186 mmol) in ethanol (3 ml) to 80° C. for 4 h. The resulting precipitate was separated by filtration and washed with ethanol (69 mg, 0.178 mmol, 96%). LC/ESI-MS: m/z 388 [M+H]$^+$; m/z=386 [M−H]$^−$; R$_t$=3.07 min.

Example 8

N-{6-[4-(4-Methylpiperazin-1-yl)pyrimidin-2-ylamino] benzothiazol-2-yl}benzamide was prepared by heating a mixture of N-(6-aminobenzothiazol-2-yl)benzamide (IM 2, 50 mg, 0.186 mmol) and 2-chloro-4-(4methylpiperazin1-yl) pyrimidine (IM 10, 40 mg, 0.186 mmol) in ethanol (3 mL) to 80° C. for 4 days. After dissolving the precipitate by addition of dimethylformamide, pTLC (dichloromethane:methanol=4.1) yielded a solid (44 mg, 0.100 mmol, 54%). LC/ESI-MS: m/z=446 [M+H]$^+$; m/z=444 [M−H]$^−$; R$_t$=2.12 min.

Example 9

N-{6-[4-(5-Methylpyrazol-3-ylamino)pyrimidin-2-ylamino]benzothiazol-2-yl}benzamide was prepared by heating a mixture of N-(6-aminobenzothiazol-2-yl)benzamide (IM 2, 35 mg, 0.13 mmol) and (2-chloropyrimidin-4-yl)-(5-methylpyrazol-3-yl)amine (IM 11, 30 mg, 0.143 mmol) in ethanol (3 mL) to 80° C. for 9 h. The precipitate was separated by filtration, washed with ethanol and dried (38 mg, 85 μmol, 66%). LC/ESI-MS: m/z=443 [M+H]$^+$; m/z =441 [M−H]$^−$; R$_t$=2.80 min.

Example 10

N-[5-(6,7-Dimethoxyquinazolin-4-ylamino)benzothiazol-2-yl]benzamide was prepared by heating a mixture of N-5-aminobenzothiazol-2-yl)benzamide (IM; 5, 30 mg, 0.111 mmol) and 4-chloro-6,7-dimethoxyquinazoline (Fluorochem, 25 mg, 0.111 mmol) in ethylene glycol (0.7 mL) to 100° C. for 2 h Brine (25 mL) and saturated sodium hydrogencarbonate solution (25 mL) were added and the product was extracted with chloroform (3×40 mL). After drying over Na$_2$SO$_4$, the solvent was removed and ethyl acetate and petroleum ether were added to the residue. Filtration yielded a yellow solid (28 mg, 60 μmol, 55%). LC/ESI-MS: m/z=458 [M+H]$^+$; m/z=456 [M−H]$^−$; R$_t$=3.20 min.

Example 11

N-[5-(Purin-6-ylamino)benzothiazol-2-yl]benzamide was prepared by heating a mixture of N-(5-aminobenzothiazol-2-yl)benzamide (IM 5, 50 mg, 0.186 mmol) and 6-chloropurine (29 mg, 0.186 mmol) in ethanol (3 ml) to 80° C. for 4 h. The resulting precipitate was separated by filtration and washed with ethanol (68 mg, 0.174 mmol, 94%). LC/ESI-MS: m/z=388 [M+H]$^+$; m/z=386 [M−H]$^−$; R$_t$=3.13 min.

Example 12

N-{5-[4-(4-Methylpiperazin-1-yl)pyrimidin-2-ylamino] benzothiazol-2-yl}benzamide was prepared by heating a mixture of N-(5-aminobenzothiazol-2-yl)benzamide (IM 5, 50 mg, 0.186 mmol) and 2-chloro-4-(4-methylpiperazin1-yl) pyrimidine (IM 10, 40 mg, 0.186 mmol) in ethanol (3 mL) to 80° C. for 4 days. Brine (25 mL) and saturated sodium hydrogencarbonate solution (25 mL) were, added and the product was extracted with chloroform (3×40 mL) and ethyl acetate (40 mL). The combined organic phases were dried over Na$_2$SO$_4$ and the solvent was removed. The residue was purified by pTLC (dichloromethane:methanol=4:1) to yield a solid (44 mg, 99 μmol, 53%). LC/ESI-MS: m/z=446 [M+H]$^+$; m/z=444 [M−H]$^-$; R$_t$=2.38 min.

Example 13

N-{5-[4-(5-Methylpyrazol-3-ylamino)pyrimidin-2-ylamino]benzothiazol-2-yl}benzamide was prepared by heating a mixture of N-(5-aminobenzothiazol-2-yl)benzamide (IM 5, 35 mg, 0.13 mmol) and (2-chloropyrimidin-4-yl)-(5-methylpyrazol-3-yl)amine (IM 11, 30 mg, 0.143 mmol) in ethanol (3 mL) to 80° C. for 9 h. The precipitate was separated by filtration, washed with ethanol and dried (32 mg, 72 μmol, 56%) LC/ESI-MS: m/z=443 [M+H]$^+$; m/z 441 [M−H]$^-$; R$_t$=2.92 min.

Example 15

N-(6-{6-Methoxy-7-[3-(4-methyl-piperazin-1-yl)-propoxy]-quinazolin-4-ylamino}-benzooxazol-2-yl)-benzamide was prepared by reaction of intermediate 1 (0.138 mM) with intermediate 7 (0.138 mM) in butanol (3 mL) under acidic katalysis (3.0 eq., 0.105 mL, 4 M HCl in Dioxane) at 110° C. The reaction was finished after 5 h. After cooling the reaction was partitioned between saturated aqueous NaHCO$_3$ solution and ethyl acetate. The layers were separated, the aqueous layer was extracted with ethyl acetate. The combined organic layers were washed neutral with water and dried with Na$_2$SO$_4$. After filtration and removal of the solvent in vacuo the product was purified by prep. HPLC.

Example 16

N-(5-{7-Methoxy-6-[3-(4-methyl-piperazin-1-yl)-propoxy]-quinazolin-4-ylamino}-benzothiazol-2-yl)-benzamide was prepared by heating a mixture of N-(5-aminobenzothiazol-2-yl)benzamide (IM 5, 35 mg, 0.13 mmol), 4-chloro-7-methoxy-6-[3-(4-methylpiperazin-1-yl)propoxy] quinazoline (IM 8, 46 mg, 0.13 mmol) and 4 M HCl in dioxane (0.09 mL, 0.39 mmol) in n-butanol (3 mL) to 110° C. for 5 h. The HCl salt of the product precipitated. It was separated by filtration and washed twice with CH$_2$Cl$_2$. No ether purification was necessary (65 mg, 0.1 mmol, 93%). LC:/ESI-MS: m/z=620 [M+H]$^+$; m/z=618 [M−H]$^-$; R$_t$=2.43 min.

Example 17

N-(5-{6-Methoxy-7-[3-(4-methyl-piperazin-1-yl)-propoxy]-quinazolin-4-ylamino}-benzothiazol-2-yl)-benzamide was prepared according to the procedure described for example 15 from intermediate 5 and intermediate 7.

Example 18

3-Chloro-N-(6-{6-methoxy-7-[3-(4-methyl-piperazin-1-yl)-propoxy]-quinazolin-4-ylamino}-benzothiazol-2-yl)-benzamide was prepared by reaction of intermediate 12 (30 mg, 58 μmol) with 3-chloro-benzoyl chloride (8 μL, 63 μmol) in a mixture of pyridine and DMF (1:1, 4 mL total) in the presence of triethylamine (100 μL, 0.71 mmol) at 60° C. The reaction controlled several times, if necessary further acid chloride was added. The reaction mixture was partitioned between saturated aqueous NaHCO$_3$ solution and DCM. After extraction with dichloromethane the combined organic layers were dried with Na$_2$SO$_4$. The solvent was removed in vacuo after filtration and the product purified by prep. HPLC (20 mg, 55% yield).

Example 19

3-Chloro-N-(5-{6-methoxy-7-[3-(4-methyl-piperazin-1-yl)-propoxy]-quinazolin-4-ylamino}-benzothiazol-2-yl)-benzamide was prepared following the procedure described for example 18 starting from intermediate 13.

Example 20

1-(4-Chloro-3-trifluoromethyl-phenyl)-3-(6-{6-methoxy-7-[3-(4-methyl-piperazin-1-yl)-propoxy]-quinazolin-4-ylamino}-benzothiazol-2-yl)urea was prepared by reaction of intermediate 12 (58 μmol, 30 mg) with 1-chloro-4-isocyanato-2-trifluoromethyl-benzene (13 mg, 58 μmol) in dichloromethane in the presence of triethylamine (5 drops). The product was purified by prep. HPLC (5 mg, 15% yield).

Example 21

1-(4-Chloro-3-trifluoromethyl-phenyl)-3-(5-{6-methoxy-7-[3-(4-methyl-piperazin-1-yl)-propoxy]-quinazolin-4-ylamino}-benzothiazol-2-yl)-urea was prepared according to the procedure described for example 20 starting from intermediate 13.

Example 22

1-(2-Methoxy-5-methyl-phenyl)-3-(6-{6-methoxy-7-[3-(4-methyl-piperazin-1-yl)-propoxy]-quinazolin-4-ylamino}-benzothiazol-2-yl)-urea was prepared according to the procedure described for example 20 starting from intermediate 12 and 2-isocyanato-1-methoxy-4-methyl-benzene.

Example 23

1-(6-{6-Methoxy-7-[3-(4-methyl-piperazin-1-yl)-propoxy]-quinazolin-4-ylamino}-benzothiazol-2-yl)-3-(2-methoxy-phenyl)-urea was prepared according to the procedure described for example 20 starting from intermediate 12 and 1-isocyanato-2-methoxy-benzene.

Example 24

1-{6-[6-(2-Hydroxy-ethylamino)-pyrimidin-4-ylamino]-benzothiazol-2-yl}-3-(2-methoxy-5-methyl-phenyl)-urea was prepared by heating a mixture of IM 14 (100 mg, 0.227 mmol) and 3-aminoethanol (1 mL) at 85° C. for 3 h. The product was precipitated by the addition of water (47 mg, 45%).

Example 25

1-{6-[6-(3-Hydroxy-propylamino)-pyrimidin-4-ylamino]-benzothiazol-2-yl}-3-(2-methoxy-5-methyl-phenyl)-urea was prepared by heating a mixture of IM 14 (100 mg, 0.227 mmol) and 3-aminopropanol (1 mL) at 85° C. for 3 h. The product was precipitated by the addition of water (42 mg, 39%).

Analytical data of compounds of formula (I) of the present invention:
| Example | Compound Structure | LC/ESI-MS: [M + H] m/z = | Rt |
|---|---|---|---|
| 1 | 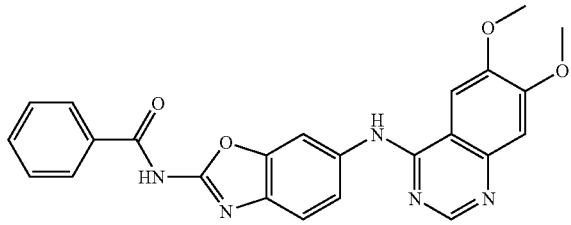 | 442 | 2.43 |
| 2 | 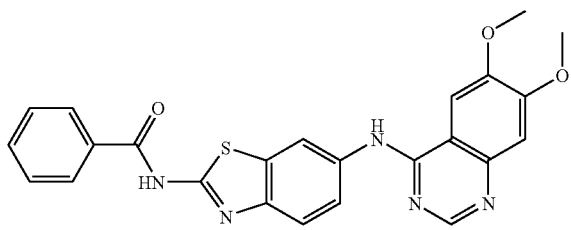 | 458 | 2.880 |
| 3 | 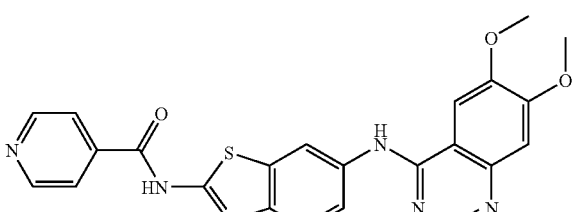 | 459 | 2.65 |
| 4 | 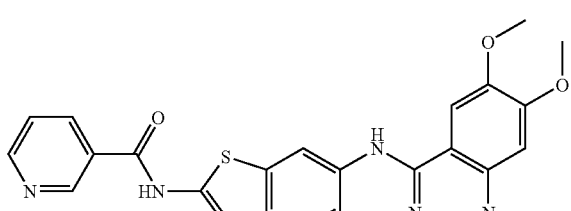 | 459 | 2.60 |
| 5 | 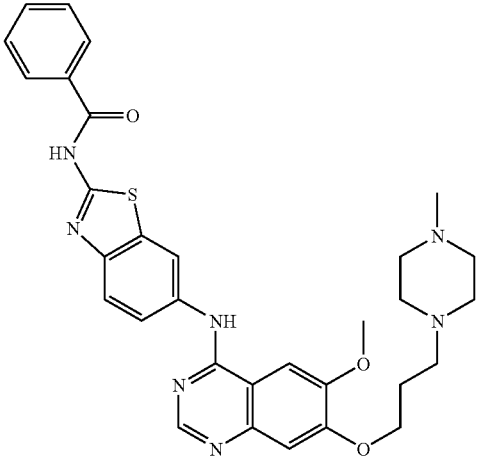 | 584 | 2.27 |

-continued
| Example | Compound Structure | LC/ESI-MS: [M + H] m/z = | Rt |
|---|---|---|---|
| 6 | 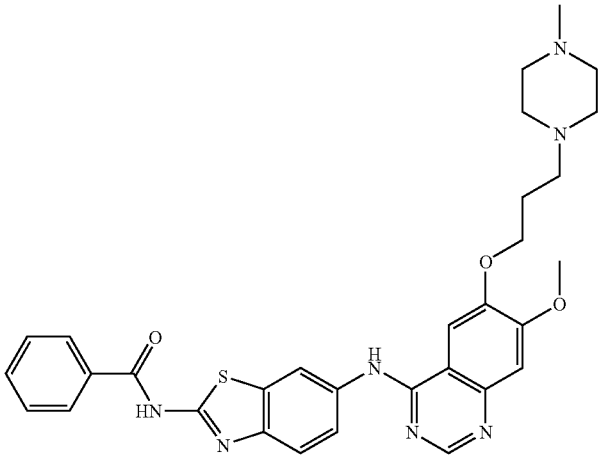 | 584 | 2.26 |
| 7 | 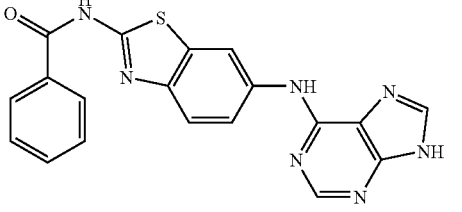 | 388 | 3.07 |
| 10 | 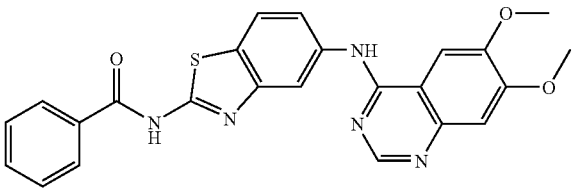 | 458 | 3.20 |
| 11 | 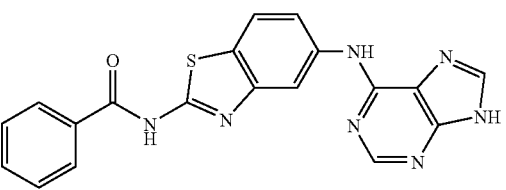 | 388 | 3.13 |
| 15 | 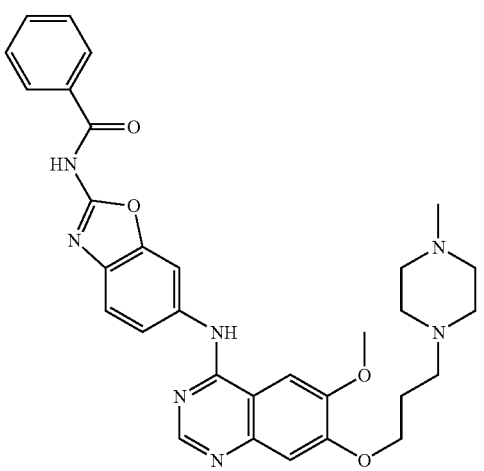 | 568 | 2.22 |

-continued
| Example | Compound Structure | LC/ESI-MS: [M + H] m/z = | Rt |
|---|---|---|---|
| 16 | 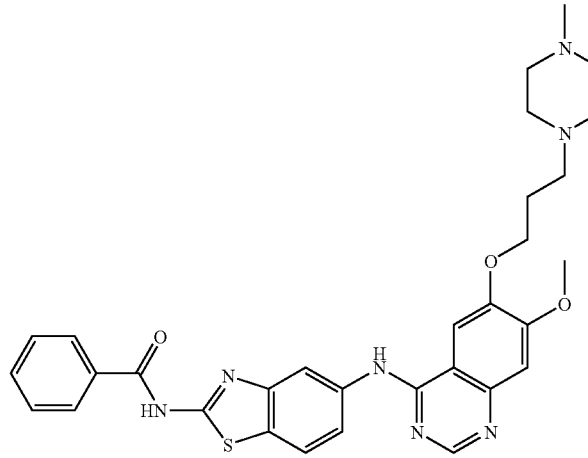 | 584 | 2.43 |
| 17 | 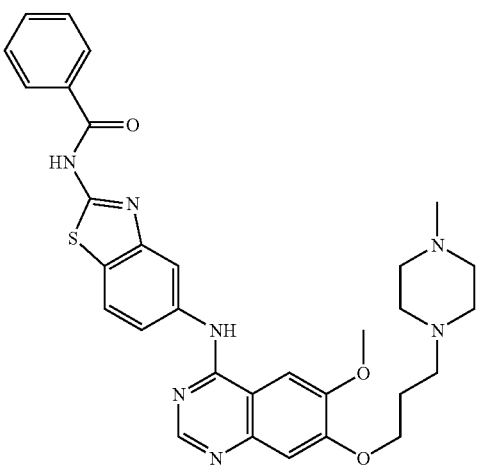 | 584 | 2.34 |
| 18 | 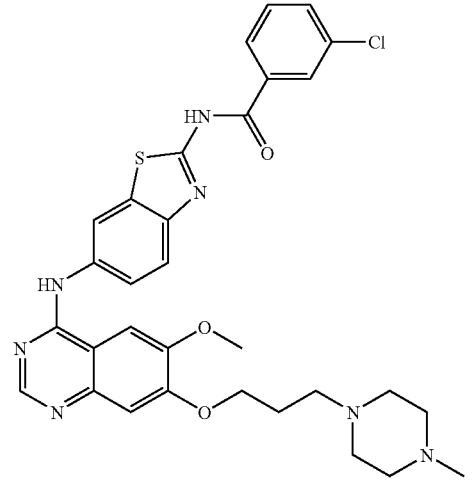 | 618 | 3.20 |

-continued

| Example | Compound Structure | LC/ESI-MS: [M + H] m/z = | Rt |
|---------|-------------------|--------------------------|------|
| 19 | 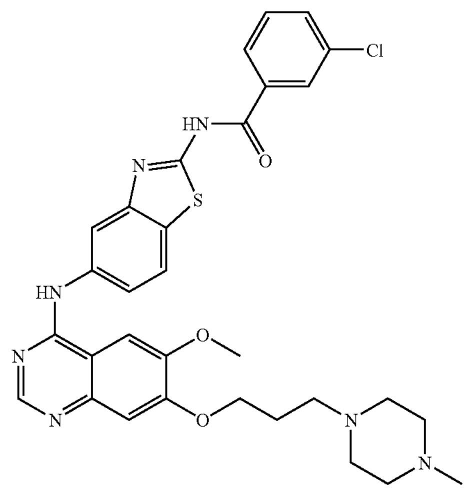 | 618 | 2.27 |
| 20 | 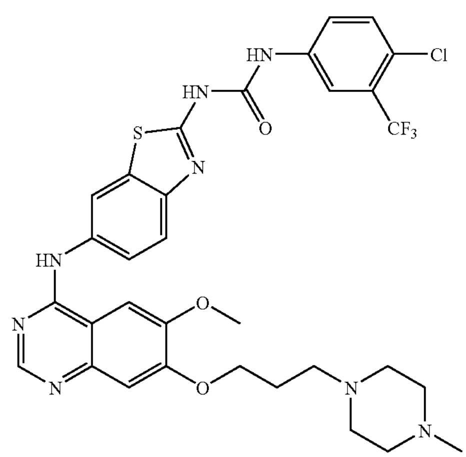 | 701 | 2.87 |
| 21 | 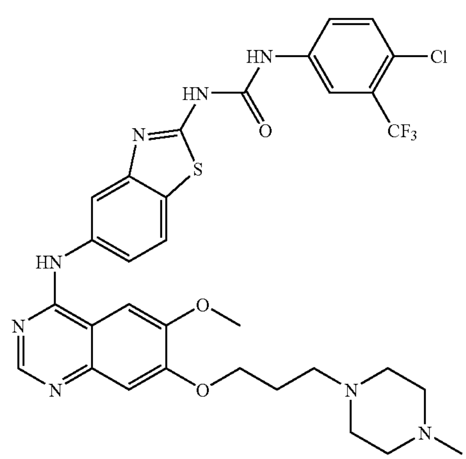 | 701 | 3.07 |

-continued
| Example | Compound Structure | LC/ESI-MS: [M + H] m/z = | Rt |
|---|---|---|---|
| 22 | 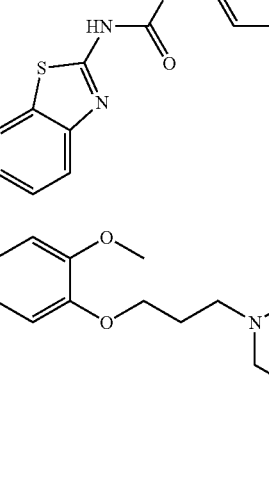 | 643 | 2.62 |
| 23 | 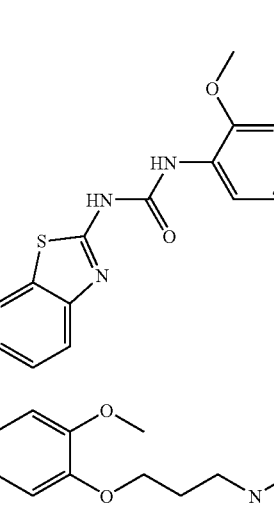 | 629 | 2.52 |

Analytical data of compounds of formula (Ia) of the present invention:

| Example | Compound Structure | LC/ESI-MS: [M + H] m/z = | Rt |
|---|---|---|---|
| 24 | 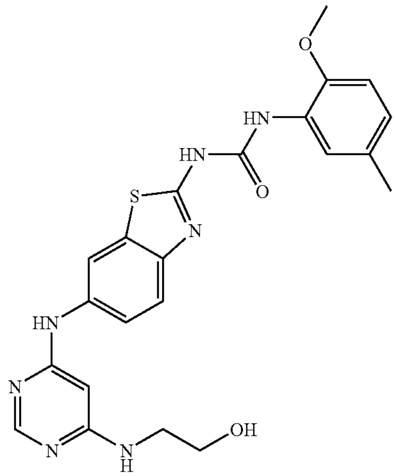 | 466 | 2.87 |
| 25 | 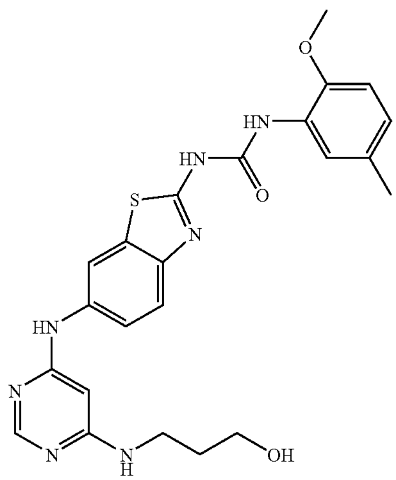 | 480 | 2.94 |

Analytical data of compounds of formula (II) of the present invention:

| Example | Compound Structure | LC/ESI-MS: [M + H] m/z = | Rt |
|---|---|---|---|
| 8 | 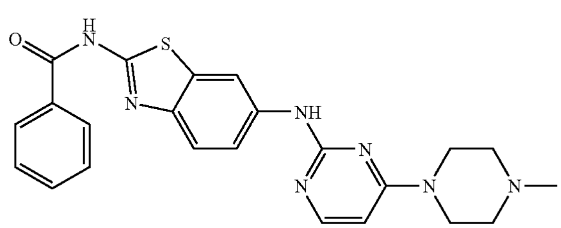 | 446 | 2.12 |

| Example | Compound Structure | LC/ESI-MS: [M + H] m/z = | Rt |
|---|---|---|---|
| 9 | 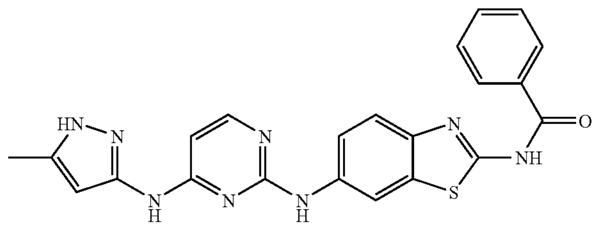 | 443 | 2.80 |
| 12 | 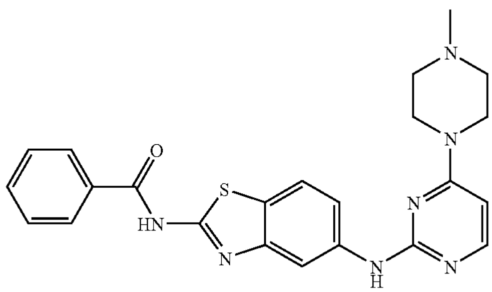 | 446 | 2.38 |
| 13 | 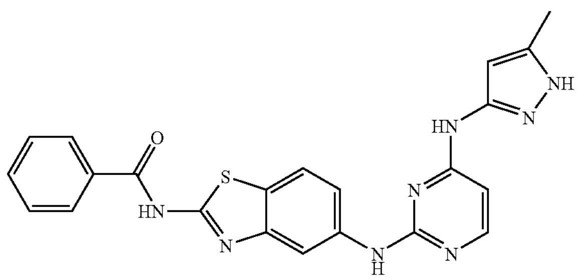 | 443 | 2.38 |

Materials and Methods

Protein Kinase Assay

The effect of the benzazole derivatives was tested on recombinant, human protein kinases. All protein kinases were expressed in Sf9 insect cells as human recombinant GST-fusion proteins or as His-tagged proteins by means of the baculovirus expression system. Protein kinases were purified by affinity chromatography using either GSH-agarose or Ni-NTH-agarose. The purity and identity of each was checked by SDS-PAGE/silver staining and by western blot analysis with specific antibodies.

A proprietary protein kinase assay ($^{33}$PanQinase® Activity Assay) was used for measuring the kinase activity. All kinase assays were performed in 96-well FlashPlates™ in a 50 μl reaction volume. The assay for all enzymes contained 60 mM HEPES-NaOH, pH 7.5, 3 mM $MgCl_2$, 3 mM $MnCl_2$, 3 μM Na-orthovanadate, 1.2 mM DTT, 50 μg/ml $PEG_{20000}$ and 1 μM [γ-$^{33}$P]-ATP (approx. 5×10$^5$ cpm per well).

The reaction cocktails were incubated at 30° C. for 80 minutes. The reaction was stopped with 50 μl of 2% (v/v) $H_3PO_4$, plates were aspirated and washed two times with 200 μl of 0.9% (w/v) NaCl. Izcorporation of $^{33}P_i$ was determined with a microplate scintillation counter. All assays were performed with a BeckmanCoulter/Sagian robotic system.

Cellular Receptor Tyrosine Kinase Assay

The effect of thiazole derivatives were tested by determining the inhibition of different receptor tyrosine kinases (RTKs) in various cell lines which expressed the following growth factor receptors: EGF-R, PDGF-R, TIE2, IGF-1R, EPHB4, and VEGF-R2. Receptor autophosphorylation was induced by specific ligands for each receptor. Stimulation of cells resulted in maximal autophosphorylation in control cells (high control) without inhibitor. Test compounds were applied to cells prior to stimulation. Cells were lysed using a standard lysis buffer preserving the distinct phosphoprotein levels. RTK-phosphorylation was quantified via sandwich ELISA using receptor-specific capture antibodies and a phosphotyrosine antibody.

Sigmoidal inhibitor curves based or relative inhibition compared with phosphorylation levels under high control conditions were generated which allowed the determination of $IC_{50}$ values for each test compound.

Cellular Aurora-B Kinase Assay

The effect of thiazole derivatives was tested in a cellular Aurora-B assay by measuring the effect of the test compounds on the endoreduplication (EndoR) of genomic DNA. Endoreduplication is detectable in cells as DNA-content higher then 4 n. Propidium Iodine (PI) was used to quantify the DNA content using a fluorescence activated cell sorter (FACS).

In the experiment, HT29 colon-carcinoma cells were treated with test compounds at different concentrations for 3 days. On day 5 cells were harvested and fixed in methanol. On day 6 cells were rehydrated and incubated with RNAse A and PI. Incorporated PI was detected by FACS measuring fluorescence emission at 650 nm upon excitation at 488 nm. For each compound concentration the percentage of EndoR-population as compared to the whole cell population was determined. For estimation of IC$_{50}$ values of Aurora-B inhibition the percentages of EndoR-populations were plotted versus compound concentrations.

Cellular Aurora-B Kinase Histone H3 Phosphorylation Assay

The effect of compounds was tested in a cellular Aurora-B assay measuring, phosphorylation of the Aurora B-substrate protein Histone H3 at Serine 10 (MisH3-pS10). Inhibition of Aurora B results in reduction of HisH3-pS10 which was detected in a specific immuno-assay.

In the experiment, HT-29 colon-carcinoma cells were seeded on day 1 and on day 2 test compounds at different concentrations were added. Cells were incubated with test compounds for 1 hour. Subsequently, Calyculin A was added for 30 min. For DELFIA®-detection (PerkinElmer) of HisH3-pS10, lysates were transferred to a microtiterplate and incubated with detecting antibody directed against HisH3-pS10 and Europium-labelled secondary anti-IgG-antibody. Emission at 615 nm was measured upon excitation at 340 nm and the percentage of inhibition was calculated for each concentration of the test compounds relative to controls without inhibitor. Mean values of MHisH3-pS10 percentage were plotted versus compound concentration for calculation of IC$_{50}$-values.

Results

The following examples show IC$_{50}$ values lower than 500 nM on at least one kinase selected from Aurora A, Aurora B, EGF-R, ERBB2, PDGFR, IGF1-R, VEGF-R2, VEGF-R3, EPHB4, Tie2, and SRC or display a beneficial activity profile by inhibiting at least two kinases from at least two different molecular mechanisms of tumor progression with IC$_{50}$ values lower than 500 nM: 1, 2, 5, 6, 9, 11, 15, 17, 18, 20, 21, 22.

The compounds of the present invention show IC$_{50}$ values lower than 10 µM in the Cellular Receptor Tyrosine Kinase Assays and/or the Cellular Aurora-B Kinase Assays.

The invention claimed is:

1. A compound of the general formula (I) or a salt thereof,

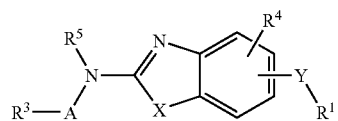

formula (I)

wherein
the substituent —Y—R$^1$ is attached to the 5- or 6-position of the benzazole;
X independently represents S, O, SO, or SO$_2$;
Y independently represents S, O, NR$^2$, SO, or SO$_2$;
A independently represents ←CO—, ←CS—, ←SO—, ←SO$_2$, ←CO$_2$—, ←CONR$^8$—, ←NR$^8$CO—, ←NR$^8$CONR$^9$—, ←NR$^8$COO—, ←NR$^8$NR$^9$CO—, ←NR$^8$OCO—, ←ONR$^8$CO—, or ←NR$^8$SO$_2$—, where ← indicates the point of attachment to R$^3$;
R$^2$ independently represents H, alkyl, cycloalkyl, —COR$^6$, —SOR$^6$, —SO$_2$R$^6$, —CN, hydroxyalkyl, haloalkyl, or haloalkyloxy;
R$^3$ independently represents H, alkyl, cycloalkyl, aryl, or heteroaryl;
R$^4$ independently represents H, —COR$^6$, —CO$_2$R$^6$, —SOR$^6$, —SO$_2$R$^6$, —SO$_3$R$^6$, —NO$_2$, —CN, —CF$_3$, —OCH$_3$, —OCF$_3$, alkyl, cycloalkyl, alkoxy, —NH$_2$, alkylamino, —NR$^7$COR$^6$, halogen, —OH, —SH, alkylthio, haloalkyl, haloalkoxy, aryl or heteroaryl;
R$^5$ independently represents H, alkyl, cycloalkyl, —COR$^6$, —SOR$^6$, —SO$_2$R$^6$, —CN, hydroxyalkyl, haloalkyl, haloalkyloxy, aryl, or heteroaryl;
R$^{6a}$ independently represents H, alkyl, cycloalkyl, —NR$^8$NR$^2$R$^9$, —ONR$^8$R$^9$, —NR$^8$OR$^9$, aryl or heteroaryl;
R$^6$ independently represents H, alkyl, cycloalkyl, —NR$^8$R$^9$, —NR$^8$NR$^2$R$^9$, —ONR$^8$R$^9$, —NR$^8$OR$^9$, aryl or heteroaryl;
R$^7$ independently represents H, alkyl, cycloalkyl, or alkoxy;
R$^8$ independently represents H, alkyl, cycloalkyl, —COR$^6$, —SOR$^6$, —SO$_2$R$^6$, haloalkyl, haloalkyloxy, aryl or heteroaryl;
R$^9$ independently represents H, alkyl, cycloalkyl, —COR$^6$, —SOR$^6$, —SO$_2$R$^6$, haloalkyl, haloalkyloxy, aryl or heteroaryl;
R$^1$ independently represents one of the following groups:

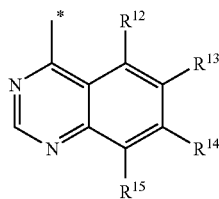 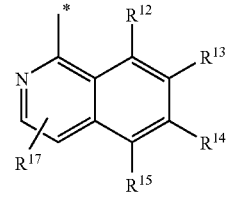

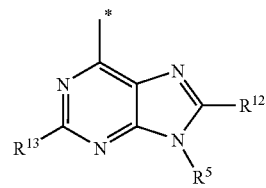

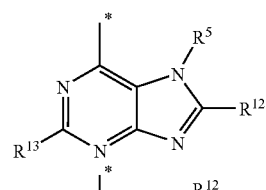

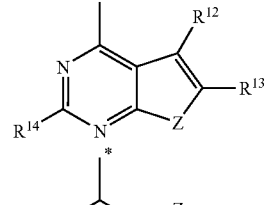

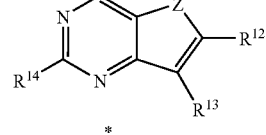

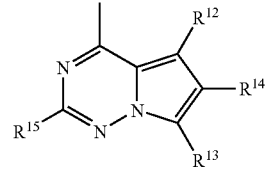 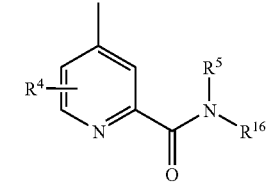

where * indicates the point of attachment;

Z independently represents O, $NR^8$, or S;

$R^{12}$ independently represents H, halogen, nitro, trifluoromethyl, alkyl, aryl, heteroaryl, $-NR^{8a}R^{9a}$, or $-X^2R^{16}$;

$R^{8a}$ independently represents H, alkyl, cycloalkyl, $-COR^{6a}$, $-SOR^6$, $-SO_2R^6$, haloalkyl, haloalkyloxy, aryl or heteroaryl;

$R^{9a}$ independently represents H, alkyl, cycloalkyl, $-COR^{6a}$, $-SOR^6$, $-SO_2R^6$, haloalkyl, haloalkyloxy, aryl or heteroaryl;

$R^{13}$ independently represents H, halogen, nitro, trifluoromethyl, alkyl, aryl, heteroaryl, $-NR^{8a}R^{9a}$, or $-X^2R^{16}$;

$R^{14}$ independently represents H, halogen, nitro, trifluoromethyl, alkyl, aryl, heteroaryl, $-NR^{8a}R^{9a}$, or $-X^2R^{16}$;

$R^{15}$ independently represents H, halogen, nitro, trifluoromethyl, alkyl, aryl, heteroaryl, $-NR^{8a}R^{9a}$, or $-X^2R^{16}$;

$R^{17}$ independently represents H, halogen, nitro, trifluoromethyl, alkyl, aryl, heteroaryl, $-NR^{8a}R^{9a}$, or $-X^2R^{16}$;

$X^2$ independently represents a direct bond, $-O-$, $-CH_2-$, $-OCO-$, carbonyl, $-S-$, $-SO-$, $-SO_2-$, $-NR^8CO-$, $-CONR^8-$, $-SO_2NR^8-$, $-NR^8SO_2-$ or $-NR^{8a}-$;

$R^{16}$ independently represents H, alkyl, cycloalkyl, $-SOR^6$, $-SO_2R^6$, $-OCH_3$, hydroxyalkyl, haloalkyl, haloalkyloxy, or one of the following groups:

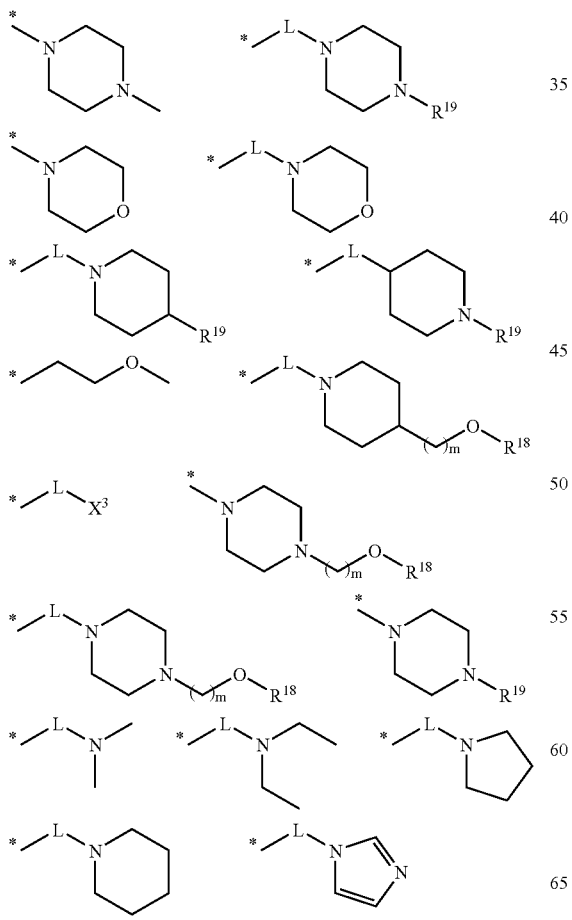

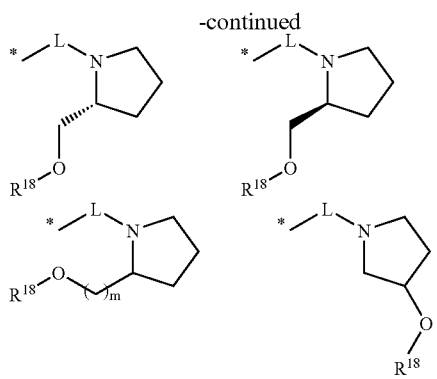

where * indicates the point of attachment;

m independently represents an integer from 1-3;

L is absent or represents a divalent linkage group selected from alkylene, cycloalkylen, heterocyclylen, arylene, or heteroarylen, wherein one or more of the ($-CH_2-$) groups may be replaced by an oxygen or a $NR^8$, and wherein one or more carbon atoms may be independently substituted by one or two substituents selected from halogen, hydroxy, alkoxy, haloalkyloxy, phosphonooxy, or phosphonooxyalkyl;

$X^3$ independently represents $-COOH$, $-COOalkyl$, $-OH$, $-SH$, $-SO_3H$, or $-SO_2NR^8R^9$;

$R^{18}$ independently represents H, phosphonooxy, or phosphonooxyalkyl;

$R^{19}$ independently represents H, alkyl, cycloalkyl, alkylamino, or alkoxy; with the proviso that the following compounds are excluded:

N-[6-(6,7-dimethoxy-quinolin-4-yloxy)-5-fluoro-benzothiazol-2-yl]-2-phenyl-acetamide, N-[6-(6,7-dimethoxy-quinolin-4-yloxy)-benzothiazol-2-yl]-2-phenyl-acetamide, N-[6-(6,7-dimethoxy-quinolin-4-yloxy)-5-fluoro-benzothiazol-2-yl]-3-phenyl-propionamide, N-[6-(6,7-dimethoxy-quinolin-4-yloxy)-5-fluoro-benzothiazol-2-yl]-2-(3-trifluoromethyl-phenyl)-acetamide, 2-(3,5-bis-trifluoromethylphenyl)-N-[6-(6,7-dimethoxy-quinolin-4-yloxy)-5-fluoro-benzothiazol-2-yl]-acetamide, 2-(2-chloro-5-trifluoromethyl-phenyl)-N-[6-(6,7-dimethoxy-quinolin-4-yl-oxy)-5-fluoro-benzothiazol-2-yl]-acetamide;

wherein an alkyl group, if not stated otherwise, denotes a linear or branched $C_1$-$C_6$-alkyl, a linear or branched $C_2$-$C_6$-alkenyl or a linear or branched $C_2$-$C_6$-alkynyl group, which can be substituted by one or more substituents R';

wherein R' independently represents H, $-CO_2R"$, $-CONHR"$, $-CR"O$, $-SO_2NR"$, $-NR"-CO$-haloalkyl, $-NO_2$, $-NR"-SO_2$-haloalkyl, $-NR"-SO_2$-alkyl, $-SO_2$-alkyl, $-NR"-CO$-alkyl, $-CN$, alkyl, cycloalkyl, aminoalkyl, alkylamino, alkoxy, $-OH$, $-SH$, alkylthio, hydroxyalkyl, hydroxyalkylamino, halogen, haloalkyl, haloalkyloxy, aryl, arylalkyl or heteroaryl;

wherein R" independently represents H, haloalkyl, hydroxyalkyl, alkyl, cycloalkyl, aryl, heteroaryl or aminoalkyl;

wherein a cycloalkyl group denotes a non-aromatic ring system containing three to eight carbon atoms, wherein one or more of the carbon atoms in the ring can be substituted by a group E, E being O, S, SO, SO$_2$, N, or NR", R" being as defined above;

wherein an alkoxy group denotes an O-alkyl group, the alkyl group being as defined above;

wherein an alkylthio group denotes an S-alkyl group, the alkyl group being as defined above;

wherein an haloalkyl group denotes an alkyl group which is substituted by one to five halogen atoms, the alkyl group being as defined above;

wherein a hydroxyalkyl group denotes an HO-alkyl group, the alkyl group being as defined above;

wherein a haloalkyloxy group denotes an alkoxy group which is substituted by one to five halogen atoms, the alkyl group being as defined above;

wherein a hydroxyalkylamino group denotes an (HO-alkyl)$_2$-N— group or HO-alkyl-NH— group, the alkyl group being as defined above;

wherein an alkylamino group denotes an HN-alkyl or N-di-alkyl group, the alkyl group being as defined above;

wherein a halogen group is chlorine, bromine, fluorine or iodine;

wherein an aryl group denotes an aromatic group having five to fifteen carbon atoms, which can be substituted by one or more substituents R', where R' is as defined above;

wherein a heteroaryl group denotes a 5- or 6-membered heterocyclic group which contains at least one heteroatom like O, N, S, wherein the heterocyclic group can be fused to another ring can be substituted by one or more substituents R', wherein R' is as defined above.

2. The compound of claim 1 or a salt thereof, wherein $R^1$ is (* indicates the point of attachment)

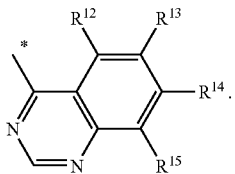

3. The compound according to claim 1 or a salt thereof, wherein X independently represents S or O; Y represents NH; A represents —CO—; $R^5$ represents H.

4. The compound according to claim 1 or a salt thereof, wherein X independently represents S or O; Y represents NH; $R^5$ represents H; A represents ←NHCO—, where ← indicates the point of attachment to $R^3$.

5. The compound according to claim 1 or a salt thereof, wherein the —Y—$R^1$ substituent is attached to the 6-position of the benzazole.

6. The compound according to claim 5 or a salt thereof, wherein $R^{12}$ and $R^{15}$ are H, and $R^{13}$ and $R^{14}$ independently represent —O-alkyl which may be substituted.

7. A compound of the general formula (Ia) or a salt thereof, formula (Ia)

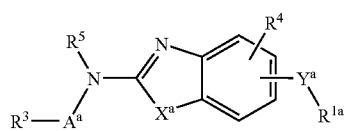

wherein
the substituent —$Y^a$—$R^{1a}$ is attached to the 5- or 6-position of the benzazole;

$X^a$ independently represents S, O, SO, or SO$_2$;

$Y^a$ independently represents S, NR$^2$, SO, or SO$_2$;

$A^a$ independently represents ←CO—, ←CS—, ←SO—, ←SO$_2$—, ←CO$_2$—, ←CONR$^8$—, ←NR$^8$CO—, ←NR$^8$CONR$^9$—; ←NR$^8$COO—, ←NR$^8$NR$^9$CO—, ←NR$^8$OCO—, ←ONR$^8$CO—, or ←NR$^8$SO$_2$—, where ← indicates the point of attachment to $R^3$;

$R^{1a}$ independently represents one of the following groups:

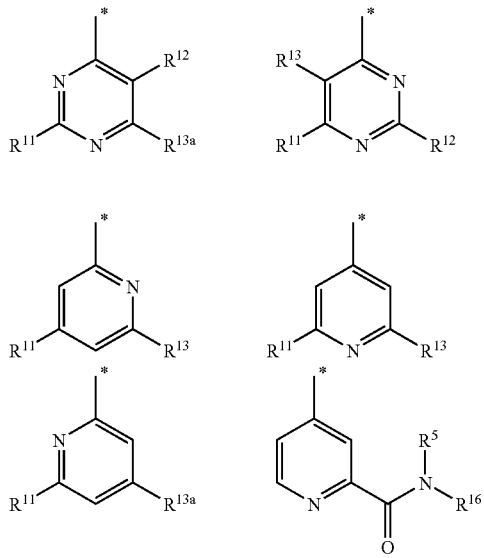

where * indicates the point of attachment;

$R^{11}$ independently represents H, —NHR$^{8a}$, or one of the groups:

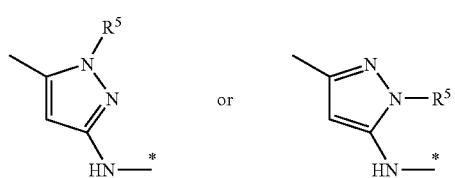

where * indicates point of attachment;

$R^{13a}$ independently represents H, halogen, nitro, trifluoromethyl, alkyl, —NR$^{8a}$R$^{9a}$, or —X$^2$R$^{16}$;

$R^2$, $R^3$, $R^4$, $R^5$, $R^6$, $R^{6a}$, $R^7$, $R^8$, $R^{8a}$, $R^9$, $R^{9a}$, $R^{12}$, $R^{13}$, $R^{16}$, or $X^2$, are as defined in claim 1.

8. A compound of the general formula (II) or a salt thereof, formula (II)

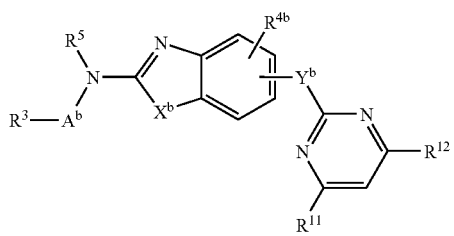

wherein
the substituent —$Y^b$— is attached to the 5- or 6-position of the benzazole;

$X^b$ independently represents S, O, SO, or $SO_2$;

$Y^b$ independently represents S, $NR^2$, or SO, $SO_2$;

$A^b$ independently represents ←CO—, ←CS—, ←SO—, ←$SO_2$—, ←$CO_2$—, ←$CONR^8$—, ←$NR^8CO$—, ←$NR^8CONR^9$—; ←$NR^8COO$—, ←$NR^8NR^9CO$—, ←$NR^8OCO$—, ←$ONR^8CO$—, or ←$NR^8SO_2$—, where ← indicates the point of attachment to $R^3$;

$R^{4b}$ independently represents H, —$SOR^6$, —$SO_2R^6$, —$SO_3R^6$, —$NO_2$, —CN, —$CF_3$, —$OCH_3$, —$OCF_3$, alkyl, cycloalkyl, alkoxy, oxyalkyl, alkoxyalkyl, —$NH_2$, alkylamine, aminoalkyl, alkylaminoalkyl, —$NR^7COR^6$, halogen, —OH, —SH, alkylthio, hydroxyalkyl, haloalkyl, haloalkyloxy, aryl or heteroaryl;

$R^2, R^3, R^4, R^5, R^6, R^{6a}, R^7, R^8, R^{8a}, R^9, R^{9a}, R^{11}, R^{12}, R^{16}, X^2$ are as defined in claims 1.

9. A composition containing a compound of claim 1 or a salt thereof and optionally an adjuvant and/or an additive.

10. A composition containing a compound of claim 7 or a salt thereof and optionally an adjuvant and/or an additive.

11. A composition containing a compound of claim 8 or a salt thereof and optionally an adjuvant and/or an additive.

\* \* \* \* \*

UNITED STATES PATENT AND TRADEMARK OFFICE
CERTIFICATE OF CORRECTION

| | |
|---|---|
| PATENT NO. | : 7,576,090 B2 |
| APPLICATION NO. | : 11/317909 |
| DATED | : August 18, 2009 |
| INVENTOR(S) | : Herz et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this

Seventh Day of September, 2010

David J. Kappos
*Director of the United States Patent and Trademark Office*